US005554501A

United States Patent [19]
Coassin et al.

[11] Patent Number: 5,554,501
[45] Date of Patent: Sep. 10, 1996

[54] BIOPOLYMER SYNTHESIS USING SURFACE ACTIVATED BIAXIALLY ORIENTED POLYPROPYLENE

[75] Inventors: Peter J. Coassin, San Juan Capistrano; Robert S. Matson, Orange; Jang B. Rampal, Yorba Linda, all of Calif.

[73] Assignee: Beckman Instruments, Inc., Fullerton, Calif.

[21] Appl. No.: 145,939

[22] Filed: Oct. 29, 1993

Related U.S. Application Data

[63] Continuation-in-part of Ser. No. 971,100, Oct. 29, 1992, abandoned.

[51] Int. Cl.⁶ .............................. C12Q 1/68; G01N 35/48
[52] U.S. Cl. .................................. 435/6; 436/63; 436/89; 436/94; 530/334; 536/25.3
[58] Field of Search .................................. 435/6; 436/94, 436/63, 89, 807; 530/334; 536/25.3

[56] References Cited

U.S. PATENT DOCUMENTS

| | | | |
|---|---|---|---|
| 4,000,102 | 12/1976 | Shima et al. | 260/23 H |
| 4,613,517 | 9/1986 | Williams et al. | 427/2 |
| 4,689,405 | 8/1987 | Frank et al. | 536/27 |
| 4,794,150 | 12/1988 | Steel | 525/54.11 |
| 4,923,901 | 5/1990 | Koester et al. | 521/53 |
| 5,011,861 | 4/1991 | Coull et al. | 521/53 |
| 5,112,736 | 5/1992 | Caldwell et al. | 435/6 |

FOREIGN PATENT DOCUMENTS

| | | |
|---|---|---|
| 2370694 | 5/1990 | European Pat. Off. . |
| 85/01051 | 3/1985 | WIPO . |
| 89/10977 | 11/1989 | WIPO . |
| 89/11548 | 11/1989 | WIPO . |
| 90/07582 | 7/1990 | WIPO . |
| 90/15070 | 12/1990 | WIPO . |
| 9015883 | 12/1990 | WIPO . |

OTHER PUBLICATIONS

Hollahan, J. R. et al. "Attachment of Amino Groups to Polymer Surfaces by Radiofrequency Plasmas" *J. Appl. Pol. Sci.* 13:807–816 (1969).

Cappello, J. et al. "The Design and Production of Bioactive Protein Polymers for Biomedical Applications" (source unknown), pp. 193–194.

Douglas, S. P., et al., "Polymer–Supported Solution Synthesis of Oligosaccharides" *J. Am. Chem. Soc.* 1991 113:5095–5097.

Wang, Y. J. et al. "A One–Sided & Hydrophilic Polypropylene Membrane Prepared by Plasma Treatment," *J. Mem. Sci.* 53:275–286 (1990).

Zhang, Yong, et al. "Single–base mutational analysis of cancer and genetic disease using membrane bound modified oligonucleotides" *Nucleic Acids Research*, vol. 19, No. 14 3929–3933.

Saiki, Randall K., et al. "Genetic analysis of amplified DNA with immobilized sequence–specific oligonucleotide probes" *Proc. Natl. Acad. Sci. USA*, vol. 86, 6230–6234, Aug. 1989.

Bentjen, Susan B. et al. "The Introduction of Alkyl, Ester, Carboxylate, Amino, Hydroxyl, and Phosphate Functional Groups to the Surface of Polyethylene" *Journal of Applied Polymer Science*, vol. 44, 965–980.

Bright, Frank V., et al. "Enhanced performance of fibre–optic immunoprobes using refunctionalized fluoropolymers as the substratum" *Analytica Chimica Acta*, 262 (1992) 323–330.

Maskos, Uwe et al. "Oligonucleotide hybridisations on glass supports: a novel linker for oligonucleotide synthesis and hybridisation properties of oligonucleotides synthesised in situ" *Nucleic Acids Research*, vol. 20, No. 7 1679–1684.

Bailey, Jerome M., et al. "Automated carboxy–terminal sequence analysis of peptides" *Protein Science (1992) I*, 68–80.

Shenoy, Narmada R., et al. "Carboxylic acid–modified polyethylene: A novel support for the covalent immobilization of polypeptides for C–terminal sequencing" *Protein Science* (1992), I, 58–67.

Wallace, R. Bruce, et al. "Solid Phase Synthesis and Biological Applications of Polydeoxyribonucleotides" (Chapter 13) pp. 631–663, Dept. of Molecular Genetics, City of Hope Research Institute, Duarte, CA 91010.

Sipehia, *Biomat. Art. Cells Art. Org.* 16(5), 955–966 (1988–1989).

*Primary Examiner*—Kenneth R. Horlick
*Attorney, Agent, or Firm*—William H. May; Janis C. Henry

[57] ABSTRACT

Disclosed herein are surface activated, organic polymers useful for biopolymer synthesis. Most preferably, aminated biaxially oriented polypropylene is used for the synthesis of oligonucleotides thereto, and these devices are most preferably utilized for genetic analysis of patient samples.

12 Claims, 5 Drawing Sheets

BIOPOLYMER SYNTHESIS USING SURFACE ACTIVATED BIAXIALLY ORIENTED POLYPROPYLENE

This application is a continuation-in-part of Ser. No. 07/971,100, filed Oct. 29, 1992, abandoned.

FIELD OF THE INVENTION

The present invention is directed to the synthesis of biopolymers or biomonomers onto, and the attachment of previously synthesized biopolymers onto, surface activated, organic polymers. The present invention finds particular usefulness in the synthesis of nucleic acids, peptides, proteins, as well as sequencing by hybridization, peptide/protein sequencing, and diagnostic evaluation at the genetic level.

BACKGROUND OF THE INVENTION

Articles and publications set forth in this patent disclosure are presented for the information contained therein; none of this information is admitted to be statutory "prior art" and we reserve the right to establish prior inventorship with respect to any such information.

Deoxyribonucleic acid ("DNA") and ribonucleic acid ("RNA") are long, threadlike macromolecules, DNA comprising a chain of deoxyribonucleotides, and RNA comprising a chain of ribonucleotides. A nucleotide consists of a nucleoside and one or more phosphate groups; a nucleoside consists of a nitrogenous base linked to a pentose sugar. Typically, the phosphate group is attached to the fifth-carbon ("C-5") hydroxyl group ("OH") of the pentose sugar; however, it can also be attached to the third-carbon hydroxyl group ("C-3 OH"). In a molecule of DNA, the pentose sugar is deoxyribose, while in a molecule of RNA, the pentose sugar is ribose. The nitrogenous bases in DNA are adenine ("A"), cytosine ("C"), guanine ("G"), and thymine ("T"). These bases are the same for RNA, except that uracil ("U") replaces thymine. Accordingly, the major nucleosides of DNA, collectively referred to as "deoxynucleosides" are as follows: deoxyadenosine ("dA"); deoxycytidine ("dC"); deoxyguanosine ("dG"); and thymidine ("T"). The corresponding ribonucleosides are designated as "A"; "C"; "G"; and "U". (By convention, and because there is no corresponding thymidine ribonucleoside, deoxythymidine is typically designated as "T"; for consistency purposes, however, thymidine will be designated as "dT" throughout this disclosure).

The sequence of the nitrogenous bases of the DNA or RNA molecule encodes the genetic information contained in the molecule. The sugar and phosphate groups of a DNA or RNA molecule perform a structural role, forming the backbone of the molecule. Specifically, the sugar moiety of each nucleotide is linked to the sugar moiety of the adjacent nucleotide such that the 3'-hydroxyl of the pentose sugar of one nucleotide is linked to the 5'-hydroxyl of the pentose sugar of the adjacent nucleotide. The linkage between the two pentose sugars is typically via a phosphodiester bond. Based upon this linkage protocol, one end ("terminus") of the nucleotide chain has a 5'-terminus (e.g. hydroxyl, phosphate, phosphates, etc.), and the other end has e.g., a 3'-hydroxyl or phosphate group. By convention, the base sequence of a nucleotide chain is written in a 5' to 3' direction, i.e., 5'-ATCG-3', or, simply ATCG.

DNA and RNA are produced internally by living animals; however, DNA and RNA can be chemically synthesized such that synthetic strands of DNA and RNA can be rapidly and efficiently produced. These strands are typically referred to as "synthetic oligonucleotides" or "oligonucleotides." A widely utilized chemical procedure for the synthesis of oligonucleotides is referred to as the "phosphoramidite methodology." See, e.g., U.S. Pat. No. 4,415,732; McBride, L. and Caruthers, M. *Tetrahedron Letters*, 24.:245–248 (1983); and Sinha, N. et al. *Nuc. Acids Res.* 12:4539–4557 (1984), which are all incorporated herein by reference. Commercially available oligonucleotide synthesizers based upon the phosphoramidite methodology include, e.g., the Beckman Instruments OLIGO 1000; the Millipore 8750™; and the ABI 380B™, 392™ and 394™ DNA synthesizers. Regardless of the protocol or the instrument, most typically synthetic oligonucleotides are "grown" on a support material, typically referred to as a "solid support". Solid supports are varied and well-known; specifics regarding solid supports will be set forth in detail below.

The importance of chemically synthesized oligonucleotides is principally due to the wide variety of applications to which oligonucleotides can be directed. For example, oligonucleotides can be utilized in biological studies involving genetic engineering, recombinant DNA techniques, antisense DNA, detection of genomic DNA, probing DNA and RNA from various systems, detection of protein-DNA complexes, detection of site directed mutagenesis, primers for DNA and RNA synthesis, primers for amplification techniques such as the polymerase chain reaction, ligase chain reaction, etc, templates, linkers, and molecular interaction studies. Recent attention in the area of oligonucleotide synthesis has focused on procedures generally referred to as Sequencing by Hybridization ("SBH"), as first disclosed by Edwin Southern (see European Patent Application No. WO 89/10977, "Analyzing Polynucleotide Sequences").

The primary repeating structures of DNA and RNA molecules can be depicted as the following nucleosides:

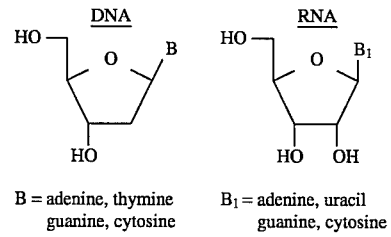

B = adenine, thymine guanine, cytosine    B₁ = adenine, uracil guanine, cytosine The key step in nucleic acid synthesis is the specific and sequential formation of internucleotide phosphate linkages between a 5'-OH group of one nucleotide and a 3'-OH group of another nucleotide. Accordingly, in the typical synthesis of oligonucleotides, the phosphite group of an "incoming" nucleotide is combined with the 5'-OH group of another nucleotide (i.e. the 5'-OH group is "phosphorylated" or "phosphitylated"). These groups must be capable of actively participating in the synthesis of the oligonucleotides. Thus, the 5'-OH groups are modified (typically with a dimethoxy trityl ("DMT") group) such that an investigator can introduce two such nucleotides into a reaction chamber and adjust the conditions therein so that the two nucleotides are properly combined; by a series of successive such additions, a growing oligonucleotide having a defined sequence can be accurately generated.

Proteins and peptides are essential components of all living cells. They are the structural elements of cell walls and cell membranes, enzymes, immunoglobulins, antibodies, transport molecules and most hormones. The building blocks of proteins and peptides are the twenty natural amino acids. Each amino acid is "encoded" by the sequential grouping of three nucleotides, referred to as a "codon". Because there are four different nucleotides and three nucleotides are required to encode an amino acid, there are 64 possible codons ($4^3$). Thus, several codons can encode for the same amino acid; for example, the codons GCG, GCA, GCT and GCC all encode for the amino acid alanine.

A series of amino acids correctly linked together via amide bonds form protein chains, and the amino acid sequence of such a protein chain ("primary structure") determines the very complex secondary and territory structures responsible for the biological functions of the proteins.

Each amino acid has an amino and carboxyl terminal, such that proteins and peptides have an amino ("N-") and a carboxyl ("C-") terminal end. The general formula of an amino acid can be depicted as follows:

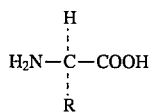

where R is one of at least 20 different side chains (for example, the side chain for alanine is a $CH_3$ group). The "$NH_2$" group is the amino group, and the "COOH" group is the carboxyl group.

As with nucleic acids, synthetic linear or branched amino acid chains can be chemically synthesized. A particularly well known procedure for the synthesis of linear amino acid chains, referred to as "solid phase peptide synthesis", was introduced by Merrifield in 1963. See generally, Barany, G. and Merrifield, R. B. (1980) in *The Peptides,* 2:1–284. Gross, E. and Meienhofer, J. Eds. Academic Press, New York. Automated peptide synthesizers which utilize solid phase peptide synthesis protocols include, for example, the ABI 430™ and 431™ the Millipore 9050 Plus PepSynthesizer™, and the Milligen 9500™ and 9600™. Typically, the C-terminal end of the first amino acid is coupled to a solid support comprising a reactive group (i.e., the site of attachment), while the N-terminal end of the first amino acid is protected with a labile protecting group (i.e., a group that can be readily removed). The side chain functional groups on the amino acids must be protected with "temporary" protecting groups. Under appropriate conditions, a similarly protected amino acid is added to the insolubilized first amino acid which has had the labile protecting group removed therefrom. By a series of successive additions, an amino acid chain can be synthesized, the final step typically being the cleavage of the chain from the solid support and the removal of the temporary protecting groups from each amino acid side chain. This leads to a biologically active protein or peptide.

Oligosaccharides are the building blocks for glycopeptides and glycolipids; glycopeptides and glycolipids can be important mediators of biological activity by interacting with cell membrane surfaces. Thus, synthetic oligosaccharides can be utilized, inter alia, to target specific cell membrane surfaces or to interfere with the natural binding of glycopeptides and glycolipids to a cell membrane surface. Synthetic oligosaccharides have recently gained notoriety for their ability to target a specific drug to a specific tissue. The solid phase synthesis of oligosaccharides has been reported using poly (ethylene glycol) monomethyl ether as the solid support. See, Douglas, S. P. et al. *J. Am. Chem. Soc.* 113: 5095–5097 (1991). See also, Rudemacher, T. W. et al. "Glycobiology" *Ann. Rev. Biochem.* 57: 785–838 (1988).

The solid supports utilized for, inter alia, nucleic acid, protein/peptide, and oligosaccharide synthesis are varied. With respect to nucleic acid synthesis, a widely utilized solid support material is controlled pore glass ("CPG"). See, for example, U.S. Pat. No. 4,458,066. Other materials include nylon, polystyrene, polyacrylamide and cellulose. Teflon™ fiber support has been described as a substrate for oligonucleotide synthesis. See, Lohrmann, R. A. and Ruth, J. (1984) *DNA* 3:122; PCT Publication WO 85/01051 (published: Mar. 14, 1985); and Molecular Biosystems, Inc. Oxidizable Solid Supports (Cat. No. OSS-01 and OSS-02). With respect to protein/peptide synthesis, such materials include, for example, cross-linked polystyrene, cellulose and polyamide resins. U.S. Pat. No. 4,923,901 describes modified membranes having bound thereto oligonucleotides and peptides. As noted, poly (ethylene glycol) monomethyl ether has been used as a solid support for oligosaccharide synthesis.

An ongoing need exists for solid supports useful in the synthesis of these types of materials. This is because the materials heretofore utilized have associated drawbacks. For example, certain supports require the use of "spacer arms" or linkers to, in effect, couple the amino acids or proteins/peptides to the solid support; typically, when such linkers are utilized, it is often necessary to block sites on the membrane where the linkers are not located, in an effect to decrease or prevent non-specific binding of the biomonomers and biopolymers to the "non-linker" locations on the support. See, for example, Zhung, Y., et al. "Single-base mutation analysis of cancer and genetic diseases using membrane bound modified oligonucleotides" *Nuc. Acids Res.* 19(14):3927–3933 (1991)(nylon). Other materials require the use of surface modification to graft onto the surface of the solid support an appropriate material which can in turn bind the biomonomers and biopolymers. See, for example, U.S. Pat. No. 4,923,901 (polypropylene). Still other materials require, for example, chemical modification of the support to provide the necessary linkages between the support and the biomonomers and biopolymers. See, for example, U.S. Pat. No. 4,458,066 (inorganic polymers). As is evident, these additional steps add the potential for errors, and hence can negatively impact upon positive analytical results, as well as significantly increasing the cost of the support.

What are needed, and hence, what would contribute to the state of the art, are materials which can be used for the synthesis of oligonucleotides and proteins/peptides which do not require such additional protocols such that the material is capable of being rapidly, efficiently and economically prepared. With an appropriate solid support method, oligonucleotides could be synthesized thereon, and the resulting product utilized for the analysis of patient sample DNA for determination of presence or absence of specific genetic mutations.

SUMMARY OF THE INVENTION

The present invention satisfied these needs by providing organic polymers useful in the synthesis of biopolymers, the organic polymers being modified with an external chemical species, the modification being accomplished by means of the application of energy in the microwave or radio-frequency bands to the organic polymer in the presence of the external chemical species. In particularly preferred embodiments, oligonucleotides complementary to regions of genes of interest are synthesized onto the polymers, and these are in turn utilized for the analysis of patient samples for the presence or absence of particular genetic mutation(s).

Preferably, the polymers are chemically inert under conditions appropriate for biopolymer synthesis and comprise a carbon backbone comprising various elemental substituents, including, but not limited to, hydrogen, carbon, oxygen, fluorine, chlorine, bromine, sulphur and nitrogen. Representative polymers include, but are not limited to, polypropylene, polyethylene, polybutylene, polyisobutylene, polybutadiene, polyisoprene, polyvinylpyrrolidone, polytetrafluoroethylene, polyvinylidene difluoride, polyfluoroethylene-propylene, polyethylenevinyl alcohol, polymethylpentene, polychlorotrifluoroethylene, polysulfones, and blends of copolymers thereof. Polypropylene is a particularly preferred polymer. For particular end uses, most particularly preferred are biaxially oriented polypropylene films.

Preferably, the external chemical species is: (1) a chemical species not previously adsorbed to the surface of the polymer; and (2) becomes a nucleophile when adsorbed to the surface of the polymer, preferably via an elevated energy state. Most preferably, the elevated energy state is a radio-frequency plasma discharge, a microwave frequency plasma discharge, or a corona discharge.

Preferably, biopolymers include, but are not limited to, nucleic acids, proteins, peptides, hormones, oligosaccharides, lipids or the synthetic analogues thereof, such as inverted nucleotides (Ortigâo, J. et al. *Antisense Res. Dev.* 2:129 (1992)), peptide nucleic acids (Egholm M. et al. *J. Am. Chem. Soc.* 114:1895 (1992)) and Meta-DNA (Hashimoto, H. & Switzer, C. *J. Am. Chem. Soc.* 114:6255 (1992)), and combinations of the above. The biopolymer synthesis is preferably accomplished by organic, inorganic, or biochemical means, and combinations thereof. Most preferably, oligonucleotides are synthesized onto the polymers, and, as noted, these are utilized for analysis of patient samples comprising DNA.

In a particularly preferred embodiment of the invention, the organic polymer is polypropylene, the external chemical species are nitrogen and hydrogen (in the form of an ammonia gas), the nucleophile is an amine, and the elevated energy state is achieved via radio frequency plasma discharge. Thus, a particularly preferred surface activated organic polymer is a polypropylene material aminated via radio frequency plasma discharge; such materials are preferably utilized for the "in-place", or "in-situ", attachment of nucleotides and/or amino acids thereto, without the need for spacer arms or linkers, and thus particularly well suited for the synthesis of oligonucleotides and/or peptides. The amine groups on the activated organic polymers are reactive with nucleotides such that the nucleotides and/or amino acids introduced thereto are covalently attached onto the surface of the polymer. For some uses, the polypropylene is most preferably in the form of a biaxially oriented film.

Such surface activated organic polymers find particular utility in the areas of, e.g., oligonucleotide, peptide, oligosaccharide, and lipid synthesis. With respect to, e.g., oligonucleotides synthesized onto such polymers, these materials find particular utility in the areas of, e.g., Sequencing by Hybridization ("SBH") and genetic analysis for purposes of medical and diagnostic evaluation. Because polypropylene is "chemically inert", problems associated with non-specific binding are substantially avoided such that detection sensitivity is significantly improved.

DETAILED DESCRIPTION OF PREFERRED EMBODIMENTS

Figure 1:
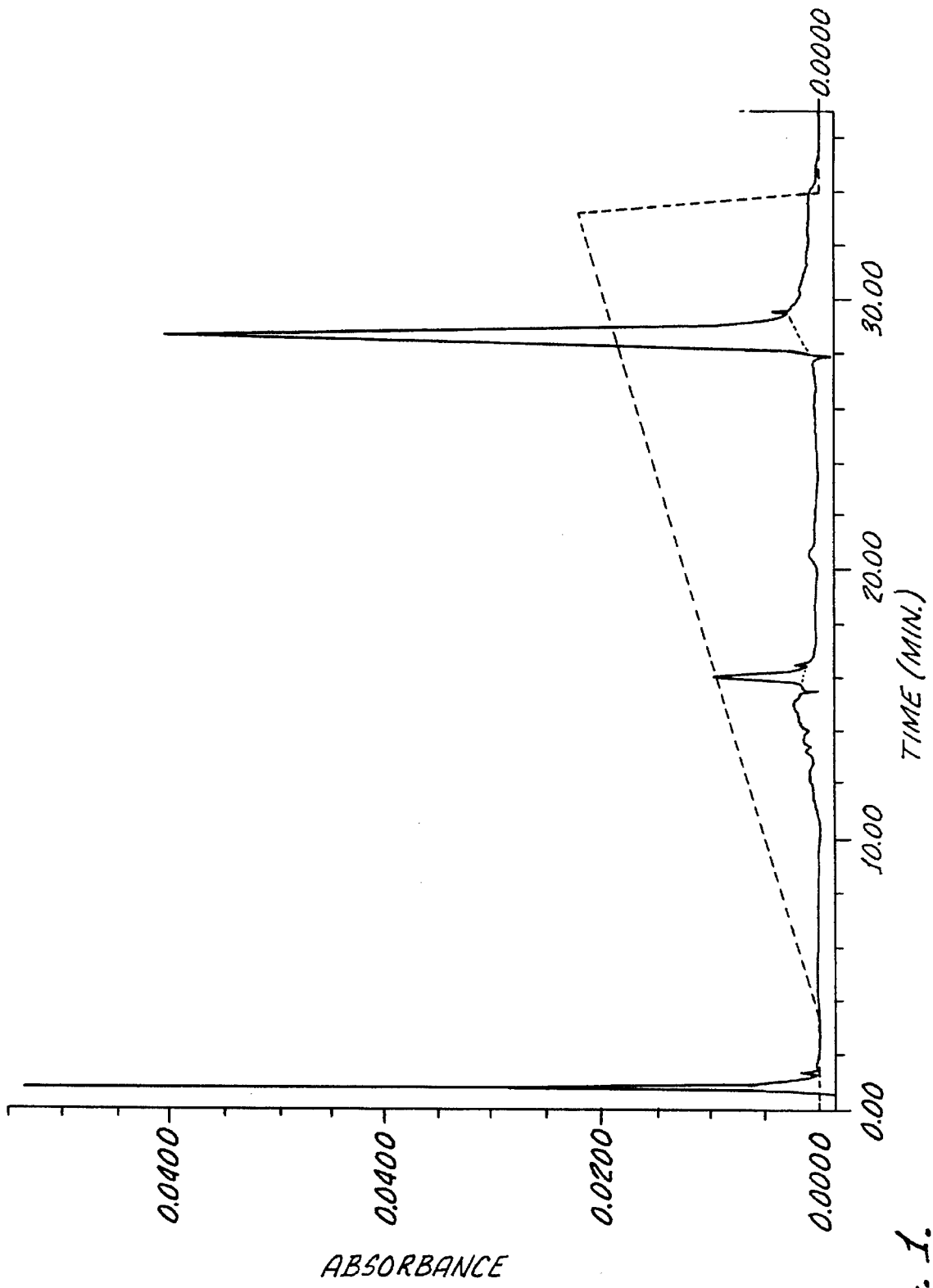
FIG. 1 is the result of High Pressure Liquid Chromatographic analysis of a cleaved 17-mer oligonucleotide (with 5'-DMT protecting group) previously synthesized directly onto aminated polypropylene.

The solid phase synthesis of biopolymers (e.g., oligonucleotides, peptides, oligosaccharides, lipids, etc.) requires, by definition, a solid support material from which the initial starting material is attached and from which the synthesis of the biopolymer is initiated. As has been noted, "The unique feature of solid phase synthesis is the solid support itself, and future improvement of the synthesis will probably depend upon finding better supports". Wallace, R. B. and Itakura, K. "Solid phase synthesis and biological applications of polydeoxyribonucleotides" Chpt. 13, *Solid Phase Biochemistry* Scouten, W. H., Ed. John Wiley & Sons (1983). As those in the art will appreciate, this statement has proven to be correct. As the chemistry involved in the synthesis of biopolymers has improved; as the need for such biopolymers, particularly oligonucleotides and peptides, has increased; and as the area of application of such biopolymers has expanded, the need for "better supports" has indeed increased.

In essence, the benefits associated with previous solid support strategies are typically also directly related to the types and number of problems occasioned by the use thereof. This is because to the degree that such materials are conducive to chemical interactions between the support material itself and the biopolymer, by that same degree the materials can interact in a non-specific manner with other materials. For example, nylon-based filters find wide-spread application in the area of DNA analysis whereby oligonucleotides are cross-linked directly to the nylon. However, nylon is very reactive with other materials such that it is typically necessary, if not essential, to chemically block any site on the nylon to which an investigator does not wish to have such "non-specific" materials bind thereto. As noted in the above-referenced Zhung article, in an effort to attempt to prevent the non-specific attachment of sample DNA to the location on the nylon membranes where amino-linker bound oligonucleotide probes were not located, it was necessary to block these highly reactive sites to avoid non-specific binding thereto. This protocol was examined in an effort to improve upon a previous procedure utilizing poly-T tails as a linker between a solid support and oligonucleotides. See, Saiki, R. K., et al (1989) *PNAS USA* 86:6230–6234. It is noted that in these procedures, the oligonucleotides are described as being synthesized "off-line" and subsequently attached to the support via an amino-linker or a poly-T tail.

In the case of "on-line" (in-situ) synthesis, the types of chemical manipulations that are required to be utilized in conjunction with the available solid supports are staggering. For example, in the case of inorganic solid supports, such as CPG, silica, glass, etc., the chemical structure of these materials creates a "rigidity" which is believed to constrain the synthesis of biopolymers. Thus, particularly in the case of CPG, it is typically necessary to utilize chemical linkers in conjunction therewith. In essence, these linkers, regardless of their chemical composition or length, are intended to provide a degree of "freedom" in the synthesis by providing a chemically "flexible" moiety which is attached to the support at one end and is capable of binding to the growing biopolymer. Without the linker, one can theoretically synthesize biopolymers, but overall yields, the rapidity of synthesis, etc. are jeopardized. As a further example of the use of inorganic materials which utilize linkers, European Patent Application No. WO 89/10977 discloses the use of glass plates having aliphatic linkers bound thereto for use in the in-situ synthesis of oligonucleotides thereon.

As those in the art will appreciate, linkers are very unpredictable. Stated again, it is not necessarily apparent which type of linker, or the lengths thereof, will be optimal for any given support material. Thus, it is typically necessary to optimize the conditions, composition and length of any given linker with any particular solid support that requires a linker.

Other supports are, in effect, not utilized as supports for the purpose of biopolymer synthesis. Rather, these materials are utilized for their ability to chemically react with other materials which in turn are conducive to such synthesis. For example, Khrapko, K. R., et. al. "Method for DNA sequencing by hybridization with oligonucleotide mixture" *DNA Sequence—J. DNA Sequencing and Mapping* 1:375–388 (1991), describe the use of an inorganic material (glass) having a polyacrylamide gel overlaid thereon such that previously synthesized oligonucleotides can be covalently linked to the polyacrylamide gel layer, but not on the inorganic material. Thus, the glass apparently functions principally as a form-support for the actual synthesis support. Similarly, in U.S. Pat. No. 4,923,901, chemically inert polymers such as polypropylene and polyethylene are described as being useful for nucleic acid and peptide synthesis, when polymer monomers with applicable functional groups are grafted onto the surface thereof.

In essence, the current state of the art runs the gamut from highly reactive materials (such as nylon) to materials which, in essence, serve as mere vehicles for linkers (i.e. glass plates).

In terms of an overall objective of biopolymer synthesis, a significant amount of energy and resources has been expended in the development of more efficient linkers or mechanisms for attaching one material to another. See, for example, Maskos, U. & Southern, E. M. "Oligonucleotide hybridizations on glass supports: a novel linker for oligonucleotide synthesis and hybridization properties of oligonucleotides synthesized in situ". *Nuc. Acids Res.* 20(7): 1079–1684 (1992).

Recognizing the correctness of Wallace and Itakura's focus on "better supports," we have embarked upon an altogether different approach and have focused our attention on the support material in toto. In so doing, we recognize that a truly superior solid support for use in biopolymer and biochemical synthesis is most preferably a material that: lacks the chemical structural rigidity of inorganic materials such that linkers can be utilized, but are not required to be used in conjunction with the support; is amenable to surface activation such that upon activation, the surface of the support is capable of covalently attaching biopolymers thereto and, in conjunction with the first criteria, is amenable to the in situ synthesis of such biopolymers; is chemically inert such that at the conclusion of biopolymer synthesis, regions on the support not occupied by the biopolymers are not amenable to non-specific binding, or when such non-specific binding does occur, these materials can be readily removed from the surface without removal of the biopolymer; and, is amenable to ease of handling and manipulation such that the material can be utilized in a variety of different contexts.

These criteria are accomplished by the use of surface activated, organic polymers which are preferably chemically inert under conditions conducive to biopolymer synthesis.

As used herein, the term "organic polymer" and "polymer" are intended to mean a support material which is most preferably chemically inert under conditions appropriate for biopolymer synthesis, and which comprises a carbon backbone comprising various elemental substituents including, but not limited to, hydrogen, carbon, oxygen, fluorine, chlorine, bromine, sulphur and nitrogen. Representative polymers include, but are not limited to, polypropylene, polyethylene, polybutylene, polyisobutylene, polybutadiene, polyisoprene, polyvinylpyrrolidone, polytetrafluoroethylene, polyvinylidene difluoride, polyfluoroethylene-propylene, polyethylenevinyl alcohol, polymethylpentene, polychlorotrifluoroethylene, polysulfones, and blends of copolymers thereof. Most preferably, the polymer is polypropylene.

As used herein, the term "surface activated" when used in conjunction with polymer is intended to mean the process of modifying a polymer such that external chemical species become adsorbed onto the surface of the polymer, whereby the chemical species are capable of chemically linking biopolymers and biomonomers to the surface of the polymer. Preferably, the chemical linking is via a nucleophile, and most preferably the nucleophile is on the surface of the modified polymer.

As used herein, the term "medium" when used in conjunction with the term "polymer" is intended to mean the physical, structural shape of the polymer; thus, "medium" can be generally defined as polymer films (i.e., polymers having a substantially non-porous surface); polymer membranes (i.e., polymers having a porous surface); polymer filaments (e.g., mesh and fabrics); polymer beads; polymer foams; polymer frits; and polymer threads. Most preferably, the polymer medium is a thread or a membrane or a film.

As used herein, the phrase "device-medium" when used in conjunction with the term "polymer" is intended to mean any device to which a polymer medium can be affixed such as, microtiter plates, test tubes, inorganic sheets, dipsticks, etc. For example, when the polymer medium is a polypropylene thread, one or more polypropylene threads can be affixed to a plastic dipstick-type device, or polypropylene membranes can be affixed to glass slides. The particular device is, in and of itself, unimportant—all that is necessary is that the polymer medium can be affixed thereto without affecting the functional behavior of the polymer or any biopolymer adsorbed thereon, and that the device intent is stable within any materials to which the device is introduced (e.g., clinical samples, etc.).

As used herein, the term "adsorbed" is intended to have a meaning ordinarily ascribed thereto in the chemical and biochemical arts. Stated again, a first material that is adsorbed onto the surface of another material becomes, in effect, a "part" of that material such that the first material is not capable of being easily removed from the surface of the other material. For example, a surface activated polymer comprises nucleophiles on the surface thereof; under appropriate conditions, biomonomers, e.g., that react with the nucleophiles will be covalently attached, and therefore adsorbed, to the surface of the biopolymer via such nucleophiles.

As used herein, the term "surface" is intended to mean a depth of no more than about 5000 angstroms (Å), preferably between about 10 and about 1000 Å.

As used herein, the term "nucleophile" is a chemical species comprising a pair of electrons which are capable of combining with an electron-deficient species. Preferably, the external chemical species becomes a nucleophile when adsorbed to the surface of the polymer. An "external chemical species" is a chemical species not previously adsorbed to the surface of the polymer. Stated again, an external chemical species becomes a nucleophile when it is adsorbed to the surface of the polymer. Preferably, an external chemical species is amenable to a plasma process. Typically, the plasma process will create ionized and radical forms of the external chemical species. Preferably, the external chemical species are selected from the group consisting of: nitrogen; oxygen; sulfur; carbon; hydrogen; argon; helium; and combinations comprising at least one of the foregoing. Nucleophilic forms of these external chemical species include, e.g., amine; hydroxyl; thiol; carboxylate; and substituents comprising at least one of the foregoing. When an external chemical species is subjected to a plasma, ionized and radical form(s) of the external chemical species result. As those in the art appreciate, under appropriate conditions, such ionized and radical form(s) can "chemically" interact with the polymer, whereas the non-ionized and non-radical form(s) thereof do not have a tendency to form chemical bonds with the polymer.

As used herein, the term "biopolymer" is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer. Related to a bioploymer is a "biomonomer" which is intended to mean a single unit of biopolymer, or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers. Additionally, as used herein, the term "initiation biomonomer" or "initiator biomonomer" is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

As used herein, "analogue" or a "synthetic analogue" when used in conjunction with a biomonomer or a biopolymer refers to natural and un-natural variants of the particular biomonomer or biopolymer. For example, an "antibody analogue" includes chimeric antibodies, monoclonal antibodies, and antibody fragments; an "amino acid analogue" includes beta-alanine; a nucleotide analogue includes inosine and dideoxynucleotides. The foregoing is not intended to be exhaustive but rather representative.

As used herein, the phrase "reverse dot blot" is meant to indicate a protocol whereby biopolymers are attached to a solid support, and the presence (or absence) of constituents in a sample material are detected via the application, and subsequent interaction (or non-interaction), of the sample to the biopolymers. As used herein, the phrase "dot blot" is meant to indicate a protocol whereby constituents in or from a sample material are attached to a solid support and biopolymer or biomonomer probes are applied thereto.

As used herein, the terms "mask" or "masking" are meant to indicate an article or a process for selectively blocking a biological, chemical or physical reaction from occurring. As a means of illustration, a mask could include a screening mechanism that is placed on top of an organic polymer prior to surface activation such that those regions of the polymer that are masked, or covered, by the screening mechanism are substantially non-surface activated after the polymer has been subjected to surface activation techniques, whereby only those areas that were not masked are substantially able to participate in, e.g., biopolymer synthesis. The terms "mask" and "masking" are not intended to be exclusively static, such that dynamic masking, i.e. a series of masking steps are utilized to selectively synthesize a variety of different biopolymers on the same activated organic polymer, is also intended to fall within the scope of this definition.

As used herein, the phrase "recognition domain" is meant to indicate a sequence of amino acids that are recognized by a receptor on a cell surface.

As used herein, the phrase "bioreactive peptide" is meant to indicate a peptide capable of eliciting a response from a cell; for example, a peptide which binds to a recognition domain on the surface of a cell is a bioreactive peptide.

As used herein, the term "seed" is meant to indicate a cell which binds to a bioreactive peptide and to which other similar cell may attach.

For convenience, the remainder of the disclosure focuses on the use of the polymer polypropylene, the chemical species ammonia, plasma protocols and the synthesis of oligonucleotides and peptides. It is to be understood that other polymers, chemical species, energy activation modes, and biopolymers are amenable to the invention disclosed herein.

Polypropylene is chemically very inert and hydrophobic; thus, polypropylene can be utilized in very corrosive environments. For example, polypropylene has good chemical resistance to a variety of mineral acids (e.g., hydrochloric acid), organic acids (e.g., formic acid, acetic acid), bases (e.g., ammonium hydroxide, potassium hydroxide), salts (e.g., sodium chloride), oxidizing agents (e.g., peracetic acid, iodine solutions) and organic solvents (e.g., acetone, ethyl alcohol, acetonitrile, etc.). Additionally, polypropylene provides low fluorescence background. Polypropylene has the following chemical structure:

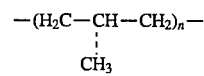

This structure is not functional vis-a-vis biopolymer synthesis; i.e., in and of itself, one cannot synthesize oligonucleotides using polypopylene as a support material. Thus, in order for polypropylene to be useful for the synthesis of biopolymers, the surface thereof must be modified via the introduction of, for example, amino groups onto the surface. An efficient, rapid and economical method for introducing such amino groups onto the surface of a polypropylene medium is by use of plasma discharge in an ammonia or organic amine containing gas.

A "plasma" is most preferably an ionized gas which gains sufficient ionization energy from an electromagnetic field. It exhibits long range electromagnetic forces and becomes a conductor of electricity. Plasma consists of a mixture of electrons, atoms, positive and negative ions and neutral free radicals. The overall electrical charge of the plasma is neutral. Plasma energy sources include, but are not limited to, direct current, alternating current, radio frequency, microwaves, shock waves and lasers. Low temperature plasma treatments include radio frequency plasma discharge ("RFPD") microwave frequency plasma discharge ("MFPD") and corona discharge ("CD"); such treatments all typically affect only the surface of a solid material to a depth of no greater than about 1000 Å, leaving the remainder of the material unmodified.

Surface interactions with plasmas usually fall into three general classes of reaction possibilities: (1) chemical species on the polymer surface can be removed from the surface; (2) external chemical species can be added to the surface of the polymer; or (3) rearrangement of bonds can occur within the surface of the polymer itself. It is possible that more than one of these reactions will occur at the same time. The principal differences between plasma discharge and alternative surface modifications (such as ionization, or α or β-irradiation, which usually penetrate deeply into the bulk of the polymer, grossly affecting the bulk characteristics thereof), are the greater chemical flexibility that can be realized in terms of the choice of reactant gas or mixtures for producing reactive species to produce various surface states, and the lack of secondary reactive species which can cause undesirable side effects.

Polypropylene can be surface activated via the introduction of amino groups thereto using RFPD, MFPD or CD in ammonia gas or other suitable amine introducing entities including, but not limited to, $C_1$-$C_{12}$ aliphatic or cyclic amines which may be primary, secondary or tertiary. The hydrocarbon chain can be straight chain, branched, saturated or unsaturated, and one or more amino groups can be attached to the hydrocarbon chain. Methyl amine, alkylamine, ethylenediamine, diaminocyclohexane are examples of such amines. Ammonia is most preferred.

In the presence of a RFPD, MFPD or CD, the most probable mechanism for the attachment of amino groups to a medium is as follows:

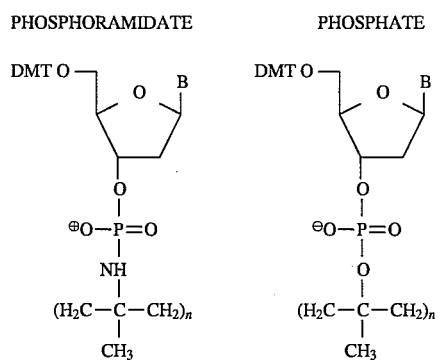

In the presence of oxygen radical, the resulting surface activated polypropylene comprises the following activated surface:

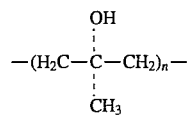

In the presence of sulfur radical, the resulting surface activated polypropylene comprises the following activated surface:

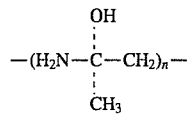

Thus, for example, using well known nucleic acid synthesis techniques, one can obtain the following adsorbed-initiation nucleotides:

PHOSPHORAMIDATE              PHOSPHATE where "A" is a protecting group and "B" represents one of the four bases. Because a chemical linker is not required to attach the biomonomer to the polymer, the initiation biomonomer is adsorbed, i.e., becomes, in effect, a "part" of the polymer itself.

Beneficially, MFPD, RFPD and CD can be efficiently controlled such that only a portion of the polymer medium need be activated. Thus, by activating only a portion of the surface, the remainder thereof continues to be chemically inert, and therein lies a benefit of the present invention. By activating only a portion of (preferably) one side of the surface of the polymer medium, only areas which are activated will be amenable to biopolymer synthesis such that at the conclusion of, e.g., in situ synthesis of oligonucleotides, substantially all of he remainder of the surface will be chemically inert. Thus, if such oligonucleotides are used as probes for a genetic trait, problems associated with non-specific binding of nucleic acid macromolecules to the surface are avoided.

Preferably, less than about 50 nmoles per square centimeter ("nmoles/$cm^2$") of the surface of the polymer medium comprises the activated chemical species, and more preferably between about 5 to 15 nmoles/$cm^2$. It is to be understood that these values are with respect to the height-by-width surface area of the polymer material; thus, in a situation where the polymer material comprises a porous surface, the foregoing values do not apply to the total surface area which, given the surface area attributed to the pores, is much greater than a height-by-width surface area. Alternately, it is preferred that less than about 15%, more preferably less than about 10%, and most preferably less than about 5% of the surface of the polymer medium comprise the activated chemical species. While this area may seem "small", or the percentages "low", these are relative values.

For instance, one could utilize a polymer medium having, e.g., a 100% activated chemical species surface. However, this could lead to problems in that all of the activated species might not be occupied by an initiation biomonomer and thus the potential for non-specific binding increases. However, as the percentage of surface activation decreases, the potential for ensuring that each activated portion of the surface is occupied by an initiation biomonomer substantially increases (particularly because the surrounding area is chemically inert).

Plasma generating devices are commercially available and applicable to the invention. A particularly preferred plasma generator is available from Plasma Science, Foster City, Calif. (Model No. PS0150E radio-frequency). Such devices are preferred because the conditions for introduction of gases, power, time of plasma discharge, etc. can be readily selected, varied, optimized and controlled. These parameters can be optimized with little experimentation, principally because the physical condition of the polymer medium is adversely affected if, for example, the amount of power (typically in watts) is too high, or the length of time of plasma discharge is too great—such adverse affects are typically manifested by the creation of a "brittle" polymer medium. Accordingly, to the degree necessary, and consistent with the parameters disclosed herein, those skilled in the art are credited with the ability to optimize the conditions for efficient surface activation of the polymer medium.

With respect to the amination of polypropylene, it is preferred that the gas comprises the following components in the following ranges: ammonia (about 99% to about 100%) and oxygen (about 0 to about 1%). Preferably, the wattage of the power supply is between about 10 and about 500 watts, more preferably between about 100 and about 400 watts, and most preferably about 200 watts. Preferably, the polypropylene and gas are subjected to the plasma discharge for less than about 10 minutes, more preferably between about 1 and about 5 minutes, and most preferably about 2 minutes. With respect to the type of plasma discharge, it is preferred that radio frequency waves be utilized; preferably these are within the range of from about 1 MHz to about 20 MHz, and most preferably about 13 MHz. With respect to microwave plasma discharge, it is preferred that the microwaves be in the range of from about 1,000 MHz to about 3,000 MHz, and most preferably about 2,000 MHz. With respect to corona discharge, it is preferred that the treatment power applied is between about 10 to about 250 watts, more preferably at the electrode between about 10,000 and 20,000 volts.

The polymer medium can be varied in accordance with the needs of the investigator. It is preferred that the polymer medium be amenable to dissection after biopolymer synthesis; however, this preference is principally based upon the intended uses of the biopolymers synthesized thereon. In the area of, e.g., nucleic acid analysis at the genetic level, we consider it absolutely essential that the testing devices be readily subjected to quality control procedures. By way of analogy, in the area of pharmaceutical manufacturing, it is relatively easy to segregate a portion (or portions) of a large-scale lot of the pharmaceutical once it is manufactured: if that portion(s) meets necessary quality assurance and quality control ("QA/QC") parameters, then, from a statistical viewpoint, the entire lot is of that same quality; if, on the other hand, that portion(s) fails the necessary QA/QC control parameters, the entire lot is suspect. The principal assumption behind this approach is that all of the parameters involved in the production of that lot were the same such that any one sample portion(s) should be representative of the entire lot. As the arena of genetic analysis expands and finds increasing utilization, similar assurances will be demanded and required.

It is with the foregoing in mind that a preference is indicated for the polymer medium bearing amenable to dissection after biopolymer synthesis.

Such a feature allows for the ability to QA/QC the biopolymer synthesized onto the polymer medium. For example, in the case of membranes, a section or sections thereof can be dissected therefrom such that detailed and stringent analytical techniques can be readily applied thereto—if such analysis indicate that, e.g., a particular oligonucleotide sequence is present, then from a statistical perspective, the entire membrane has that sequence.

Dissection of the polymer medium also allows for the generation of multiple media, each comprising the defined biopolymer. These can then be dissected and one piece from each medium can be affixed to a unitary device-medium. Thus, for example, a plethora of dipsticks can be readily created, each dipstick comprising several different polymer media sections comprising specific biopolymers; thus, the conditions for synthesis of any particular biopolymer is identical and such biopolymer is amenable to QA/QC protocols.

While the needs of the investigator will determine the specific parameters involved in the capability of dissection, we prefer to utilize, in the case of membranes, polypropylene having a thickness of between about 80 to about 100 μm, and in the case of threads, polypropylene having a diameter of about 0.001 inches. In the case of membranes, dissection can be readily accomplished with any severing device (e.g., scissors). In the case of threads, it is preferred that these be dissected with a device which can "seal" the ends at the location of the cut, i.e., a laser, an ultrasonic device or a hot-knife; this preference is predicated upon a practical concern, to wit, threads are composed of entwined fibers such that when the thread is cut, the fibers can become disassociated from each other. (The fibers themselves can, of course, be utilized directly, but threads are preferred because they are somewhat easier to manipulate; however, this is, again, a function of the desires of the investigator).

Pursuant to a particularly preferred embodiment of the invention, biaxially oriented polypropylene film (BOPP) is employed as a solid-phase activated substrate to support the synthesis of oligonucleotides. The substrate may suitably comprise an array or ordered grid, upon which the reagents necessary to perform oligonucleotide synthesis are applied either manually or mechanically. For automated mechanical application of reagents, it is presently preferred to employ reagent dispensing means comprising isolation valves which achieve a low-dead volume, non-cross contaminating configuration for delivering the reagents. Such reagent dispensing means are disclosed in, e.g., U.S. patent application Ser. Nos. 07/936,976, abandoned and 07/909,232, abandoned, which have been commonly assigned to the assignee of the present invention and are incorporated by reference herein. Alternatively, other automated synthesis systems may be modified to accomplish reagent dispensing to a polypropylene film substrate as described herein.

Radio-frequency plasma aminated polypropylene membranes and films have been proposed to be suitable substrates for synthesis of oligonucleotides in the form of an array using mechanical reagent dispensing means. However, attempts to synthesize such arrays using microporous membrane substrates resulted in unsatisfactory performance because of chemical leakage between reagent dispensing channels, loss of physical durability and increased fluorescence background. Microporous membrane substrates also proved to be far too fragile; they were easily torn during attempts to remove them from the mechanical reagent dispensing means and fell apart after repeated use. Following chemical synthesis, the membranes also appeared to exhibit an enhanced fluorescence background.

Pursuant to this particularly preferred embodiment of the invention, BOPP films have replaced membranes for use, e.g., in the synthesis of oligonucleotides using mechanical reagent dispensing means. BOPP films are durable and easily removed from the mechanical reagent dispensing means without any signs of damage after repeated use. The BOPP films also satisfy the need for a low fluorescence substrate material. Finally, BOPP film satisfies the need for a non-porous substrate which forms a seal between the channel walls of the mechanical reagent dispensing means, thus preventing the leakage of chemicals into adjacent channels.

Biaxially oriented polypropylene film substrates for use, e.g., in the synthesis of oligonucleotides are available commercially; in addition, suitable films may be readily prepared in a manner well known in the art. Suitable films include those available from Catalina Plastics, Calabasas, Calif. or Mobil Chemical Company, Films Division, Pittsford, N.Y. under the trade designations Bicor B and Bicor 100LBW. These films may generally be characterized as high clarity, translucent films of a nominal thickness of from about 0.65 to about 2 mils. Typical films are reported as having the following characteristics according to ASTM D882: tensile strength of about 19,000 to about 21,300 lb/sq in (MD) and of about 29,000 to about 38,700 lb/sq in (TD); and elongation at break of about 150 to about 162% (MD) and about 45 to about 60 (TD). The films are also reported to have a Gardner Gloss according to ASTM D2457 on the order of about 90 and a Gardner Haze according to ASTM D1003 on the order to about 1.3 to about 2.5. Further details concerning the characterization of exemplary films may be found in, e.g., the brochures "Bicor 100LBW Oriented Polypropylene Film, Developmental Typical Values (Dec. 1, 1991)" and "Bicor B Biaxially Oriented Polypropylene Film, Typical Values (Aug. 1, 1987)" available from Mobil Chemical Company, both of which are hereby incorporated by reference. Of course, these values are intended as exemplary of the characteristics of suitable films, and should not be regarded as critical to the present invention; those skilled in the art would readily be able to identify other films suitable for use in accordance with the present invention.

All polypropylene films are significantly aminated by the process of the present invention. When cast, melt blown and BOPP films were compared in their ability to serve as substrates for oligonucleotide synthesis using mechanical reagent dispensing means, however, only BOPP film was found to be an entirely suitable support for the synthesis of hybridizable oligonucleotides. The reason(s) for the failure to cast and blown films to work in this application have not been fully delineated at this time. Solvent permeation is suspected as one significant factor, as all the cast and blown films turned opaque or were hazed when heated in ammonia (28%) at 70° C. or in deionized water. The use of fast deprotection reagents at room temperature with films other than BOPP films was also unsuccessful.

The biaxially oriented polypropylene (BOPP) film is more durable than microporous membranes and offers a lower fluorescent background. BOPP film also provides better solvent resistance and is optically clearer than cast or melt blown polypropylene films. As a consequence, BOPP film is most particularly preferred as a support for oligonucleotide synthesis, in particular when using mechanical reagent dispensing means.

In order to characterize the properties of films for possible use in oligonucleotide synthesis, a number of films made of nylon, PVDF and polypropylene were tested. The best results were obtained with clear, non-porous biaxially oriented polypropylene films. Porous polypropylene membranes, as well as other porous membranes, gave high background signals, and at least a significant proportion of this background is likely due to scattering effects that cannot be filtered out sufficiently by the optical system in the DNA sequencer.

Evaluation of virgin film for dot blot hybridization analysis indicated its suitability in that application for low fluorescence detection. In preliminary studies on background fluorescence and detection sensitivity, a dilution series of infrared labeled oligonucleotides was spotted onto films and dried. A 1:2 dilution series of oligonucleotide (lacZ200) labeled with an infrared fluorescent dye was spotted onto clear, non-porous biaxially-oriented polypropylene film and air dried. The sheets were fixed between a glass plate sandwich which would normally hold the sequencing gel. Signals were detected using a LI-COR Model 4000L DNA sequencer. Signal from 1 µl spots containing 1600 fmol down to 0.1 fmol were clearly visible. The signal gain was set to 800, and the signal offset to 50. Normal offset settings for acrylamide gels would be 200–250; this clearly indicates the significantly lower background fluorescence from the substrate.

Spots corresponding to 100 attomoles of primer were clearly seen with the arrangement as described. With different alignments signals from dots at even lower concentrations could also be seen, although then some dots at higher concentration were out of alignment. Clearly, 100 attomoles is not an absolute limit. For example, a 2-dimensional scan system would allow signal integration over the entire spot area and a reliable determination of signal to noise ratios.

In a hybridization experiment using as target single stranded M13mp18 DNA, an 18-mer oligonucleotide corresponding to the lacZ-gene from nucleotide 200 to 217 was used as probe. A 1:2 dilution series of single stranded M13mp18 DNA was spotted onto a clear polypropylene film, air dried and UV cross-linked. After hybridization with infrared labeled probe at 37° C. in SDS buffer [Church & Kieffer-Higgins, *Science* 240:185 (1988)] and washing, the film was scanned in the LI-COR Model 4000L DNA sequencer. Positive hybridization signals from 100 fmol to 0.05 fmol M13 target DNA were clearly seen. The negative control contained 10 fmol plexB6 plasmid DNA; it gave a very faint signal, indicating that hybridization and washing stringency were not ideal. Signal gain and offset were 800 and 150, respectively.

As little as 50 attomoles of target DNA were clearly detected; this would correspond to $(5 \times 10^{-17}$ moles $\times 10^{10}$ g/mole=) 0.5 µg of lacZ-DNA. In this case, the probe was 5'-labeled, and thus carried only one fluorochrome. For cDNA mapping, probes of 300–1500 bp would typically be used; these may carry 10–100 dye molecules per DNA molecule, and thus a higher sensitivity would be achieved.

The disclosed polymers are particularly well suited for the direct synthesis of, e.g., oligonucleotides and peptides thereon. Beneficially, a variety of commercially available nucleic acid synthesizers are available, including the Beckman Instrument OLIGO 1000. Focusing on aminated polypropylene membranes or threads, immediately following the amination process (or after removal from storage), the materials can be incorporated directly into the reaction chamber of the nucleic acid synthesizer; because of the versatility of such materials, they can be readily manipulated within the chambers, i.e. loosely "rolled" in the case of membranes, or loosely inserted in the case of threads. Beneficially, synthesis of oligonucleotides can proceed directly onto the aminated polypropylene, and, owing to the "activated" nature of the amine groups, these oligonucleotides are covalently attached directly to the polypropylene ("cleavable" links or spacer arms can, of course, be utilized such that the oligonucleotides are amenable to removal; active esters of succinate nucleosides are preferred as these are susceptible to "cleavage" by ammonia).

Such derived oligonucleotides are ideally suited for utilization in genetic screening analyses. I.e., by utilizing aminated polypropylene comprising oligonucleotides, where the oligonucleotides are complementary to either the wild-type or mutation(s) sequence of a gene of interest, prepared patient samples can be screened for the presence or absence of the sequence of interest. It is preferred that the length of oligonucleotides chemically synthesized for use in such genetic analysis be up to about 250 bases in length, preferably between about 5 and about 100 bases, more preferably between about 8 and 30 bases, and most preferably about 16 bases. These lengths are to be construed as relative to the conditions under which the genetic analysis is conducted. For example, at room temperature (at which temperature we prefer to conduct the analysis) the most preferred length is 16 bases; at lower temperatures, shorter (i.e. 8-mers) can be utilized.

The skilled artisan is readily credited with understanding methodologies for preparing genomic samples from patients for analysis. Sample DNA can be readily obtained from, e.g., clinical samples (i.e., tears, semen, vaginal secretions, whole blood, serum, plasma, skin scrapes, etc.) and readily prepared by a variety of techniques which are available to the skilled artisan. Typically, a primary goal of these techniques is to purify the nucleic acids to a sufficient degree such that extraneous materials which might otherwise interfere with the eventual amplification (e.g., by the polymerase chain reaction) of the nucleic acids of interest are removed. Using serum as an example, preparation of the nucleic acids generally can comprise the following steps: incubate the serum for 1 hour at 70° C. with proteinase k (Boehringer Mannheim) at 2.5 mg/ml in 25 mM MOPS (pH 6.5), 2.5 mM EDTA and 0.5% SDS. This is followed by the following extractions: phenol extraction and ether extraction. This is followed by ethanol precipitation. See, e.g., A. Larzul, et al. *J. Heptol.* 5:199–204 (1987). As noted, other protocols and techniques are readily available for such purification.

Following such purification it is (typically) necessary to amplify the particular genomic region of interest. This can be readily accomplished using techniques such as the polymerase chain reaction ("PCR") and primers directed to the particular region of interest. The skilled artisan is credited with the ability to appreciate and understand the application of such amplification techniques to the genomic sample, as well as the parameters involved therein (such as selection of primers which will substantially ensure amplification of a gene segment or region of a nucleic acid sequence comprising a gene).

As will be further appreciated by the skilled artisan, because the DNA sample, by definition, comprising two complementary strands of DNA, amplification techniques such as PCR will generate sets of complementary amplicons (an "amplicon" is one set of strands of the amplification product, i.e. complementary "amplicons" are the resulting product of a PCR amplification). A suggested approach for increasing sample binding to oligonucleotides covalently attached to aminated polypropylene is to remove one of these sets from the reaction mixture prior to analysis; this has the effect of decreasing competition for hybridization of the complementary amplicons to each other. For this approach, only one of the amplicon sets is subjected to screening with the aminated polypropylene-oligonucleotide device. One approach to segregation of the amplicon sets involves manipulating the primers. For example, one set of primers can be biotinylated, and the other set can be, e.g., labelled for detection. Thus, after amplification, the biotinylated amplicons can be "removed" from the sample using, e.g., avidin-coated beads. This has the effect of maintaining substantially only labelled amplicons in the solution. The label, of course, can be utilized for detection purposes after the labelled amplicons are "screened" with the aminated polypropylene-oligonucleotide device.

Following such amplification, the sample material can be presented to the aminated polypropylene-oligonucleotide device which comprises an oligonucleotide having a sequence complementary to the labelled amplicons. Because a preferred application of the aminated polypropylene-oligonucleotide devices is screening genomic samples for genetic mutations, the stringency conditions (i.e. the conditions which allow hybridization and dehybridization to occur, including but not limited to: temperature, ionic strength, chemical conditions, time, and the nature of the sequences) are important. I.e., for mutations including only one change in nucleic acid sequences (vis-a-vis the wild-type, or "normal" sequence), it is very likely that in screening for a mutational sequence, even the normal sequence will readily hybridize to the complementary oligonucleotide. Thus, removal of such "non-specific" hybridization is essential. For example, this can be accomplished using a series of washings with decreasing salt concentrations, which has the effect of essentially removing substantially all of the non-specifically hybridized materials before removing substantially all of the specifically hybridized materials.

Because of the criticality of ensuring that only complementary sequences are detected, it is our current preference that an "historical" de-hybridization analysis be conducted so that we can "track" the de-hybridization of the sample nucleic acid sequences from the aminated polypropylene-oligonucleotide device over time and stringency conditions—by comparing the de-hybridization patterns of non-complementary and complementary sequences as they are removed from the aminated polypropylene-oligonucleotide device, we have ascertained that the patterns are substantially different such that an accurate assessment of "correct" hybridizations can be conducted. This historical analysis can be utilized for creating a "yes/no" stringency protocol for specific genetic analysis. For example, if a specific known mutation provides a specific known "historical" de-hybridization pattern, then if this pattern is obtained for an unknown sample, that sample comprises that specific mutation.

In essence, we subject the hybridized material to a decreasing salt gradient using high performance liquid chromotography ("HPLC") techniques, while continuously monitoring the loss of signal (indicative of de-hybridization) over time. As will be set forth in detail below, we have experimentally determined that distinct differences in such de-hybridization patterns can be ascertained, such that accurate determinations as to the presence or absence of defined sequences can be made. For the analysis of genomic DNA using oligonucleotides which are synthesized directly onto, e.g., aminated polypropylene, such analysis may be readily conducted as indicated above.

The genomic DNA typically comprises a gene or portions thereof. As used herein, the term "gene" is accorded the definition typically utilized by those in the art. The genomic sample can be from any source containing DNA, including, but not limited to, plants, vertebrates, invertebrates, virus sources, etc.

Oligonucleotides having different sequences can be synthesized onto the polymer medium using various "masking" protocols, such as those described in Maskos, U. and Southern, E. M. "Parallel analysis of oligodexyribonucleotide (oligonucleotide) interactions". *Nuc. Acids. Res.* 20(7): 1675–1678 (1992). For example, in the case of oligonucleotides, the initiation biomonomer applied to the entire surface of a polymer medium may be adenosine, while in only one quadrant of the medium, the nucleotide cytidine is added, the other three quadrants being masked, followed by the addition of nucleotide thymidine to one half of the entire medium, the other half being masked, and over the entire polymer medium the nucleotide guanine is added. Thus, in the first quadrant, the tetramer ACTG is present; the one half exclusive of the first quadrant includes the trimer ATG; and the other half includes the dimer AG. Such a material can be utilized for genomic analysis or for screening for genetic mutations which include various alleles. For example, there are at least 95 different nucleic acid sequences that can give rise to the gene which encodes for the disease cystic fibrosis. Thus, a single polymer device medium can be generated with 95 different biopolymers having different sequences thereon, each of the biopolymers being generated in accordance with a masking protocol as described above.

Alternately, one can synthesize different biopolymers onto different polymer mediums and combine these onto a single polymer device. For example, in the case of membranes, various sections from different polymer media comprising different oligonucleotides can be affixed to a single device. The benefit of this approach is that one can more readily quality control a portion of the polymer medium comprising the biopolymer such that the quality of a device comprising a portion of that polymer medium can be assured. In the case of cystic fibrosis, e.g. 95 separate polymer media (or a sub-population thereof) comprising 95 different oligonucleotides can be utilized, with each being dissected and portions from each being subjected to quality control procedures. Thereafter, these 95 media can be combined onto one (or several) unitary device medium.

The disclosed polymers can also be utilized for the parallel analysis of oligonucleotides, or "Sequencing by Hybridization" ("SBH"). One of the earliest and practical approaches to SBH is disclosed by Edwin M. Southern in PCT Publication No. WO 89-10977, "Analyzing Polynucleotide Sequences". See also, Maskos & Southern, supra (hereinafter "Southern SBH"). According to the Southern SBH protocol, many different oligonucleotides are synthesized onto the surface of a solid support and then utilized to carry out parallel hybridizations with sample nucleic acid sequences; the oligonucleotides are synthesized in situ which ensures uniformity of yield of the oligonucleotides. Beneficially, carrying out hybridization to all the different sequences on the same surface in a single analytical run results in identical experimental conditions for every individual oligonucleotide. Surface activated polymer medium as disclosed herein is directly applicable to SBH protocols. Surface activated polymer media are also applicable to the preparation of polymers utilizing photoremovable protecting groups. See, PCT Publication No. WO 90/15070, "Very large scale immobilized peptide synthesis".

The disclosed surface activated polymers are particularly suited for in situ biopolymer synthesis for "reverse dot blot" protocols. For example, in certain of the protocols described above, a series of oligonucleotides having different defined sequences are synthesized directly onto a surface activated polymer (or synthesized "off-line" and attached to the polymer). Thereafter, a sample suspected of containing a polynucleotide having a sequence complementary to one of the oligonucleotides is applied thereto. Detection can be accomplished via a labelling scheme that provides for labelling of the polynucleotide prior to analysis (direct labelling) or after hybridization (indirect labelling). Because the investigator knows the physical location of the different oligonucleotides on the polymer medium, the presence of a label at a specific location provides information as to both the presence and the sequence of any material from the sample that has hybridized to the aminated polypropylene oligonucleotide device.

Additionally, the disclosed surface activated polymer materials can also be utilized in conjunction with linkers and spacer arms for the synthesis of biopolymers. These can be amenable to either non-cleavage or cleavage protocols for non-removal or removal of the synthesized biopolymer from the polymer support. Linkers and spacer arms applicable to the synthesis of biopolymers, particularly oligonucleotides and peptides, are well known and varied and will not be discussed herein in detail. Thus, the disclosed polymer materials can be used for the synthesis of, e.g., oligonucleotides or peptides which can in turn be cleaved from the support and utilized in any of a variety of contexts as set forth above.

The disclosed surface activated, organic polymers are also applicable to protein/peptide sequencing. As those in the art appreciate, protein sequencing, unlike protein synthesis, is directed to the determination of the amino acid sequence of a particular protein; the amino acid sequence of a particular protein can then, in turn, be utilized for, e.g., chemical synthesis of that protein or determination of a general or optimal nucleic acid sequence of codons which will encode for the amino acids of the protein. A well known procedure for protein sequencing is referred to as "Edman degradation." See, Edman, P. and Henschen, A. (1975) in: *Protein Sequencing Determination* (Needleman, S. B. ed.) pp. 232–279. Springer-Verlag, Berlin, Heidelberg, N.Y. Briefly, the Edman degradation process involves the cleavage of amino acid residues, one at a time, from the N-terminus of the peptide, and identification thereof as phenylthiohydantoin derivatives. This procedure is well characterized and will not be set forth in detail herein. Automated protein and peptide sequencers are commercially available; exemplary is the Porton LF 3000 Protein Sequencer (Beckman Instruments, Inc.)

Beneficially, a protein to be sequenced can be covalently attached to a surface activated, chemically inert organic polymer using, e.g., 1,4 phenylene diisothiocyanate ("PDITC"); however, any moiety capable of binding to the surface of the polymer and a protein can be utilized. The coupling reaction can proceed as follows:

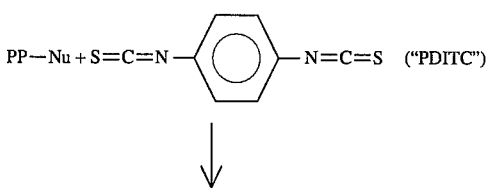

-continued

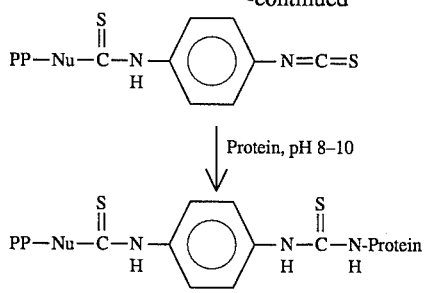

where: "PP-Nu" is polypropylene comprising a nucleophile adsorbed on the surface thereof.

The protein, being covalently attached to the polymer, can then be efficiently sequenced using, e.g., Edman degradation protocols.

Another application for the disclosed surface activated, chemically inert organic polymers can be directed to the covalent attachment of biomonomers such as avidin, avidin derivatives, biotin, and biotin derivatives. Such materials have a plethora of applications—particularly preferred is sequestering biotinylated or avidin-linked macromolecules, respectively. As those in the art appreciate, avidin is a glycoprotein having four binding sites specific for biotin; the binding affinity between biotin and avidin is both very strong and non-covalent. The utility of avidin, for example, attached to such a polymer is varied—as an example, such a material can be utilized to standardize the resulting sequence reaction of the amplification of a polynucleotide containing sample using, e.g., the PCR. For example, biotinylated primers (specific to a first region of a target sequence) are added to a polymer device medium having avidin covalently coupled thereto; thereafter, second, labelled primers (specific to a second region of the target), polymerase enzyme, and nucleotide triphosphates are added to the bound primer and the PCR reaction is initiated. By controlling the amount of avidin attached to the polymer, the amount of biotinylated primer is "controlled", such that elongated, labelled strands which result form the PCR reaction are standardized, and these can then be analyzed utilizing, e.g., conventional slab gel electrophoresis techniques.

The surface activated, organic polymers can also be utilized for cell adhesion and cell growth/propagation for example, in devices used for mammalian cell culture, artificial skin grafts and prosthetic devices exhibiting tissue and blood compatability. For example, bioreactive peptides directed to specific cell recognition domains can be synthesized onto the disclosed polymers, and samples comprising a variety of cells can be applied thereto, whereby those cells comprising the recognition domains can selectively attach thereto. Yamada, K. M., "Adhesion Recognition Peptides," *J. Bio. Chem.* 266:20 12809–12812 (1991), describes a variety of bioreactive peptides and the cells comprising recognition domains specific for such domains. For example, the adhesive glycoprotein fibronectin is involved in a variety of biological processes, particularly in mediating cell attachment and cell migration. Fibronectin is bound by several cell surface receptors; peptide sequences of fibronectin which are recognized by such receptors include Arg-Gly-Asp ("RGD") and Leu-Asp-Val ("LDV"). Thus, a series of biopolymers comprising one or more RGD peptides can be synthesized onto the disclosed polymers to, e.g., mediate cell attachment thereto. For example, Pierschbacker and Ruoslahti, *Nature* 309:30–33, 1984 (and cited references), first isolated and characterized a peptic digest fragment of fibronectin containing the cell attachment domain. A 30-amino acid synthetic peptide was prepared which carried the cell attachment promoting activity. The domain was further delineated to a tetrapeptide (RGDS) that promoted the attachment of rat kidney fibroblasts when attached via a 6-carbon atom spacer arm to Sepharose beads but not when the RGDS tetrapeptide was coupled to protein-coated plastic plates. The authors suggested that this lack of activity might be due to a decrease in accessibility of cells to the attachment domain or because of poor coupling efficiency to the protein-coated plastic surface. To alleviate this problem, Cappello and Crissman, *Polymer Preprints* 31: 193–194, 1990, utilizing recombinant genetics, inserted a 10-amino acid sequence of fibronectin that contained the RGD domain into a segment of the amino acid sequence encoding the crystalline region of the Bombyx mori silk fibroin protein. A high molecular weight copolymer SLP-F containing repeat sequences of the RGD recombinant peptide was immobilized onto nitrocellulose filters and promoted the attachment of african green monkey kidney epithelial cells. The supports disclosed herein can be utilized in an efficient manner to achieve these types of end-results.

Preferably, bioreactive peptides are synthesized using a spacer arm to spatially distance the bioreactive peptides from the surface of the polymer. Such spacer arms are preferably about 50 atoms in length, more preferably about 20 atoms in length, and most preferably about 6 atoms. A preferred spacer arm is hydrophilic. Preferably, the bioreactive peptide sequence is repeated along a biopolymer comprising other non-bioreactive peptide sequences; this is preferred because an increase in the number of bioreactive peptide sequences increases the probability that the recognition domains of a cell will bind to the bioreactive peptide. Preferably, the bioreactive peptide sequence is repeated at least about 30 times within a biopolymer, more preferably about 15 times along the biopolymer, and most preferably about 10 times. It is preferred that the distance between any two bioreactive peptide sequences be at least about 1 amino acid residue, more preferably about 3 and most preferably about 9.

EXAMPLES

The following examples, which are neither intended nor to be construed as limiting, are directed to a particularly preferred embodiment of the invention—the amination of polypropylene, followed by the direct synthesis of oligonucleotides thereon, for use in the analysis of samples comprising nucleic acid sequences, for an indication of the presence of non-conforming sequences, i.e. mutations; and the direct synthesis of peptides thereon.

I. MATERIALS, METHODS, INSTRUMENTS AND SPECIFIED OLIGONUCLEOTIDES

A. Reagents

1) OLIGO 1000 DNA Synthesizer

Synthesis of oligonucleotides was accomplished using Beckman Instruments, Inc. BINARY-PAK™ phosphoramidites (dA(Bz) - Part No. 337737, dC(Bz) - Part No. 337738, dG(iBu) - Part No. 337739, T- Part No. 337746); DNA Synthesis Reagent Kit (Oxidize - Part No. 337732, DEblock - Part No. 337733, Cap 1 - Part No. 337734, Cap 2 - Part No. 337735); ACtivate Reagent (Part No. 338284) and Cleavage and Deprotection Kit (Part No. 337742).

2) Hybridization Buffer

All chemicals were at least of ACS grade. Hybridization buffer consisted of 6XSSPE/0.01% sodium dodecyl sulfate. 6XSSPE was prepared by dilution of 20XSSPE (per liter: 3M NaCl; 0.2M NaH$_2$PO$_4$; 0.02M EDTA; adjusted to pH 7.4 with 10N NaOH) to achieve 6X, followed by addition of 0.01% SDS (v/v) thereto.

3) D-HAS™ Gradient Buffer

D-HAS™ gradient buffer consisted of 2XSSPE/0.01% SDS (i.e., utilizing 20XSSPE stock, diluting to 2XSSPE, and addition of 0.01% SDS (v/v).)

4) Radiofrequency Plasma Reagents

Electronic grade anhydrous ammonia (99,995% purity) was obtained from Liquid Air Corporation (Walnut Creek, Calif.) under the brand name ALPHAGAZ™. Ultra high purity argon gas (99.999%) was also obtained from Liquid Air under the same brand name.

B. Polymer Device Media

Polypropylene membrane filter sheets (21.5 cm×26.6 cm, 0.2µm pore size) were obtained from Gelman Sciences Ann Arbor, Mich. under the brand name METRICEL™. Polypropylene threads (0.010 inch diameter) were obtained from Blue Mountain Industries, Blue Mountain, Ala. (Product No. MP69). Polypropylene film (1.2 mil) was obtained from Catalina Plastics and Coating Corporation (Calabasas, Calif.).

C. Commercially Available Protocols

1) Polymerase Chain Reaction ("PCR")

Amplification of specified DNA macromolecules was accomplished using PCR protocols using a Perkin-Elmer Cetus GeneAmp™ DNA Amplification Reagent Kit with AmpliTaq™ (Part No. N801-0055). Manufacturer instructions were followed.

2) Primer Biotinylation

5'-biotinylated primers for PCR amplification were made using Biotin-ON™ phosphoramidite (Clonetech Laboratories, Inc., Palo Alto, Calif. Part No. 5191). Biotinylated primers were not purified prior to utilization. Manufacturer instructions were followed.

3) Primer Labelling

Primers for PCR amplification were 5'-labelled with $\gamma P^{32}$ (Amersham, United Kingdom) using USB Cloned T4 Polynucleotide Kinase reagents. Manufacturer instructions were followed.

4) Probe Labelling 615 fluorescein probe was labelled with Fluorescein-ON phosphoramidite at the 5' end (Clonetech, Cat. No. 5235-1). Manufacturer instructions were followed.

5) Sulfo-SDTB Analyses—Amine Content, Quantitative

Amine content on polypropylene device media was determined, inter alia, using the Sulfo-SDTB Assay (Pierre Chemical; Product No. 28610X). Quantitation was achieved by measuring the release of DMT cation from the device media under acidic aqueous conditions. The amount of DMT generated was estimated from the extinction coefficient at 498 nm of 70,000 cm$^{-1}$ M$^{-1}$ or from standard curves (ΔOD 498 nm vs. Sulfo-STDB standards). Manufacturer instructions were followed with the exception that 6N HCl was used to release DMT cation into solution.

D. Additional Analytical Protocols

1) Ninhydrin Analysis—Amine Content, Qualitative

Qualitative analysis of aminated polypropylene was conducted by ninhydrin analysis; ninhydrin, a heterocyclic compound, complexes with amine groups and during the complexation process, a color change, from yellow to a deep blue, occurs. Approximately 1–3 drops of each of the following solutions were added serially to putative aminated polypropylene material: A - potassium cyanide/pyridine (0.01M KCN/98 ml pyridine); B - 500 mg ninhydrin/10 ml butanol; C - 80 mg phenol/20 ml butanol. This was followed by heating of the materials at 110° C. for about 2 min, followed by qualitative observation of color.

2) DMT Analysis—Amine content, Quantitative

Quantitative determination of amination of polypropylene was accomplished using a modification of the procedure set forth in Reddy, M. P. et al. "An efficient procedure for the solid phase tritylation of nucleosides and nucleotides." *Tetrahedron Letters* 28/1: 23–26 (1987). Amine groups react with dimethoxytrityl (DMT) chloride in the presence of tetra-n-butylammonium perchlorate/2,4, 6-collidine in dichloromethane; upon acid treatment, DMT cation is released and can be measured spectrophotometrically at 501 nm. Results can be presented as OD units/cm$^2$ of aminated polypropylene.

The protocol was as follows: aminated polypropylene was suspended in equimolar solution (0.5M) of dimethoxytrityl chloride (Aldrich, St. Louis, Mo.) and tetra-n-butylammonium perchlorate (Fluka, City, State) in dry dichloromethane containing 2,4,6-collidine. The reaction was completed within between about 15 to 30 minutes. The aminated polypropylene was removed and washed thoroughly with dichloromethane. Dry aminated polypropylene was thereafter suspended in 10 ml of 2% trichloroacetatic acid in dichloromethane (w/v); the presence of an orange color indicated the presence of DMT cation, and this was quantified spectrophotometrically ($\lambda$max–501 nm, $\epsilon$=76,000).

E. Instruments

1) Radio Frequency Gas Glow Plasma Discharge

A Plasma Sciences Instrument Model 0150E was utilized to generate a radiofrequency gas glow discharge in the presence of ammonia gas.

The amination process consisted of the following steps: a base pressure of 0.1 torr was established within the chamber at the initiation of, and between each, amination process, under a continuous vacuum sweep operation. Thereafter, anhydrous ammonia was introduced for 4 min to obtain a chamber pressure of about 0.25 torr. This was followed by application of RF-power at 200 watts for 2 min in the presence of the anhydrous ammonia gas. Following discontinuation of RF-power, the chamber was maintained in ammonia gas for an additional two minutes at the same pressure. This was followed by the introduction of argon gas into the chamber for 10 min at about 0.25 torr. Finally, the chamber was returned to atmospheric conditions under a slow vent to on for about 1 min.

2) Automated DNA Synthesizer

Synthesis of oligonucleotides was performed on a Beckman Instruments, Inc. (Fullerton, Calif.) OLIGO 1000 automated DNA synthesizer using phosphoramidite-based chemistry protocol. Aminated polypropylene was utilized for the solid support material. Homo- and hetero-oligonucleotides of various lengths were synthesized in accordance with manufacturer instructions.

3) Capillary Gel Electrophoresis ("CGE")

Capillary electrophoresis analysis of oligonucleotides was performed on a Beckman Instruments, Inc. P/ACE™ 2000 high performance capillary electrophoresis system. A 27 cm, 100 µm i.d., column (Polymicro Technologies, Inc., Phoenix, Ariz.) was utilized; polymerized polyacrylamide gel column was prepared in-house using 10% T. Samples were loaded onto the columns via the electrokinetic injection method (7.5 kV; 3.0 sec.); separation was conducted at 300 V/cm for 10–30 min, depending on oligonucleotide length. Tris-hydroxymethyl amino methane ("TRIS")-borate (pH 8.3) was utilized as the running buffer. Absorbance detection was in the range of from 0.01 to 1.0 $OD_{260nm}$/ml, depending principally on the length of the oligonucleotide.

4) High Pressure Liquid Chromatography ("HPLC")

HPLC analysis of oligonucleotides was conducted on a Beckman Instruments, Inc. System Gold™ HPLC Programmable Solvent Module 126 equipped with a diode array detector module 168 and autosampler 507 (20 µl injector loop). C18 Ultrasphere™ HPLC column (Beckman, Part No. 244254; 3 µ particle ODS, 4.6 mm×7.5 cm) was utilized. Bottle A contained 0.1M ammonium acetate, pH 6.8; Bottle B contained HPLC-grade acetonitrile. The system was operated in a gradient mode as follows (flow rate=1 ml/min): 0–3 min - 100% Bottle A, 0% Bottle B; 3–33 min - 100% Bottle A to 30% Bottle A/ Bottle B.

5) Breadboard Dynamic Hybridization Analysis (D-HAS™) System

In order to analyze the progressions of probe-target disassociation over time, a breadboard Dynamic Hybridization Analysis (D-HAS™) System was constructed. For the D-HAS™ analyzer used herein, a Beckman Instruments, Inc. System Gold™ HPLC Programmable Solvent Module 126 equipped with a modified 171 radioisotope detector was utilized; the modification consisted of replacing the flow cell with a ⅛ inch o.d./ 1/16 inch i.d. fluoronated ethylene propylene copolymer tubing. This tubing allowed for insertion of aminated polypropylene-oligonucleotides having labelled sequences of interest hybridized thereto therein, and this material was in turn "sandwiched" between 2 polypropylene screens. This arrangement allowed for the flow of Disassociation Buffer through the modified flow cell—thus, as disassociation of the labelled sequence from the aminated polypropylene oligonucleotide occurred, the number of radioactive counts decreased, thus providing a continuous tracking of the disassociation of the probe from the target. Bottle A contained D-HAS™ gradient buffer and Bottle B contained 0.01% SDS. The D-HAS™ System was operated in a gradient mode as follows: 0–2 min - 100% Bottle A (1 ml/min); 2–22 min - 0% -100% Bottle B (2 ml/min); 22–24 min - 100% Bottle B (2 ml/min); 24–26 min - 0% - 100% A (2 ml/min).

6) Charged Coupled Device ("CCD") Camera

For detection of fluorescently-labelled probe, a Photometrics Metachrome 2 CCD Array camera (Tuscon, Ariz.) in conjunction with Photometrics Nu200 Camera Controlled Software Rev. 2.0. was utilized. Laser source was an argon ion laser, 457–514 nM (OmniChrome, Chino, Calif.).

D. Oligonucleotide Sequences

Oligonucleotides utilized throughout the Examples had the following sequences (for ease of presentation, the Examples will refer to the oligonucleotides by the listed identifiers):

1. TARGET A (SEQ ID NO. 1):

3'-CCA CAT TTC GGT TGT G-5'

The 3' end of Target A was directly synthesized to the aminated polypropylene (i.e. no "linker" was utilized).

2. P23 (SEQ ID NO. 2):

5'-GGT GTA AAG CCA ACA C-3'

P23 is a labelled complement to Target A (SEQ ID No. 1)

3. P24 (SEQ ID NO. 3):

5'-GGT GTA A<u>G</u>G CCA ACA-3'

P24 is a labelled "complement" probe to Target A with the exception of the underlined base, G (this base should be an A).

4. P37 (SEQ. ID NO. 4):

5'-GGT GTA AA..CA ACA C-3'

P37 is a labelled "complement" probe to Target A with the exception of a two base deletion ("..") which should be "GG".

5. TARGET A61 (SEQ ID NO. 5):

3'-T TTA TAG TAG AAA CCA-5'

The 3' end of Target A61 was directly synthesized to the aminated polypropylen.

6. TARGET A70 (SEQ ID NO. 6):

3'-T TCT TTT ATA GTA GAA-5'

The 3' end of Target A70 was directly synthesized to the aminated polypropylene.

7. CFTR Exon 10, Normal (SEQ ID NO. 7):

5'-G TTT TCC TGG ATT ATG CCT GGC ACC ATT AAA GAA AAT ATC ATC TTT GGT GTT TCC TAT GAT GAA TAT AGA TAC AGA AGC GTC ATC AAA GCA TGC CAA C-3'

8. CFTR Exon 10, ΔF508 (SEQ ID NO. 8):

5'-G TTT TCC TGG ATT ATG CCT GGC ACC ATT AAA GAA AAT ATC ATT GGT GTT TCC TAT GAT GAA TAT AGA TAC AGA AGC GTC ATC AAA GCA TGC CAA C-3'

9. CFTR Exon 10 PCR Primer, Sense (SEQ. ID. NO. 9):

5'-G TTT TCC TGG ATT ATG CCT GGC AC-3'

This primer was biotinylated at the 5' end. 10. CFTR Exon 10 PCR Primer, Antisense (SEQ ID NO. 10): 5'-G TTG GCA TGC TTT GAT GAC GCT TC-3'

This primer was labelled at the 5' end.

11. Cleavable Target 17-mer/Qualitative (SEQ. I.D. NO. 11):

3'-TCA GCT ACC GTA AAT GT-5'

12. SAM 125 (SEQ. ID. NO. 14):

3'-AAG GAC CTA ATA CGG-5'

The 3' end was directly synthesized to aminated polypropylene film.

13. 615 Fluorescent Probe (SEQ. ID. NO. 15):

5'-GTT TTC CTG GAT TAT GCC TGG GAC

The 5' end of the probe was labelled with the fluorescein label; the underlined portion of the probe is complementary to SAM 125

EXAMPLE I

Amination of Polymer Device Media

Polypropylene membrane filter sheets and films were subjected to the RF amination procedure as delineated above. Following plasma amination, approximately 1 cm×1 cm edge cuts of the sheets and films were qualitatively analyzed for amine content by the ninhydrin reaction: non-aminated ("virgin") polypropylene control sheets and films evidenced no color change (i.e. the color remained yellow); aminated polypropylene sheets evidenced a blue color, indicative of amine groups present on the polypropylene sheets. The remainder of the sheets and films were stored at room temperature (in dark) in polyethylene bags, heat sealed using an electric wire impulse heat sealer. Prior to oligonucleotide synthesis, sheets and films were quantitatively analyzed for amine content by Sulfo-SDTB: virgin polypropylene evidenced about 0 to 1 nmoles/cm$^2$; polypropylene membrane subject to RF treatment was determined to comprise between about 5 to 30 nmoles/cm$^2$.

Polypropylene threads were subject to the RF amination procedure as delineated above, with two exceptions: substantially linear threads were placed upon the glass plates and held in-place at the ends thereof using an adhesive tape, or threads were coiled around a cylinder core of polypropylene open mesh material, followed by attachment of the cores (via the ends thereof) to the glass plates using an adhesive tape. Approximate lengths of 6–18 cm of threads were utilized for determination of amination. For qualitative analysis, virgin polypropylene thread did not evidence a blue color when subjected to ninhydrin testing protocols, while polypropylene threads subjected to the RF treatment evidenced the desired blue color. Quantitative testing (via Sulfo-SDTB) indicated that virgin polypropylene threads had an amine surface content of between about 0 to 2 nmoles/cm$^2$; polypropylene threads subjected to RF treatment evidenced an amine content of between about 5 to 30 nmoles/cm$^2$.

Masking of polypropylene sheets (21.5 cm×26.6 cm) was accomplished by placing such sheets on the glass plate within the RF instrument and overlaying the sheet with a 30 cm×30 cm polypropylene mesh filter screen (Spectra/Mesh Los Angeles, Calif., Prod. No. 146410, 1000 µm ×1000 µm nominal mesh opening). Plasma amination was conducted as delineated above. Qualitative testing for amine "patterning" (i.e. the presence of amine groups corresponding to the nominal mesh openings) was conducted using Sulfo-SDTB reagent, followed by rinsing in distilled water, followed by holding the sheets over fumes of concentrated hydrochloric acid. A "checkered" pattern resulted where the unmasked areas had an orange color (indicative of the presence of amine groups) while the areas beneath the mesh portion (masked area) was white (indicative of the absence of amine groups). The same sheet was then rinsed in distilled water, methanol and acetone, followed by air drying. Thereafter, a 30 dyne-cm blue dye wetting Tension Test System Kit No. 5 (Select Industrial Systems, Waukesha, Wis.) was applied to the polypropylene sheet; the area covered by the mesh adsorbed blue dye, indicating that this area was hydrophobic (i.e. amine groups absent), while the unmasked areas remained white in appearance, indicating that this area was hydrophilic (i.e. amine groups present).

EXAMPLE II

Determination of Oligonucleotide Presence on Aminated Polypropylene

Determination of the efficiency of oligonucleotide synthesis onto aminated polypropylene of Example I was predicated upon HPLC and CZE analysis of oligonucleotides synthesized onto the material and cleaved therefrom.

It is important that the support material allow for substantially identical synthesis on the surface thereof—i.e., if the support material allows for variation in synthesis, oligonucleotides having different lengths may be synthesized thereon.

An efficient means for determining the quality of the synthesized material is by HPLC and/or CZE analysis of the synthesized material. If the support material allows for consistent and efficient synthesis, then the material that was synthesized thereon, removed, and subjected to HPLC and/or CGE analysis should be expected to generate a single peak. I.e., there are no, or substantially minor, "contaminants" present these being indicative of oligonucleotides not having the correct sequence length and composition.

Prior to oligonucleotide synthesis, and owing to the objective of analyzing the synthesized material, a linker group was added to the aminated polypropylene. Specifically, the aminated polypropylene was condensed with the active ester of nucleoside succinate; this was followed by the addition of other nucleosides. As is appreciate, the succinate portion is amenable to "cleavage" using ammonia.

17-mer oligonucleotides (SEQ ID NO. 11) were synthesized directly onto aminated polypropylene sheets (0.5 cm×1.5 cm) which were hand-rolled and loosely packed into a needle-tip reaction column of a Beckman Instruments OLIGO 1000 DNA Synthesizer; aminated polypropylene threads (about 20 cm in length) were similarly utilized. Following synthesis of the 17-mer oligonucleotides, the oligonucleotides were cleaved from the supports with NH$_4$OH(28%) for 1 hr. at room temperature, followed by deprotection with NH$_4$OH(28%) for 1 hr. at 80° C. Released oligonucleotides were then analyzed by HPLC and CGE techniques under the parameters set forth above. Results were presented in FIG. 1 (HPLC) and FIG. 2 (CGE) for oligonucleotides synthesized onto polypropylene sheets (results for polypropylene threads yielded substantially identical results; these results are not provided herein).

Figure 2:
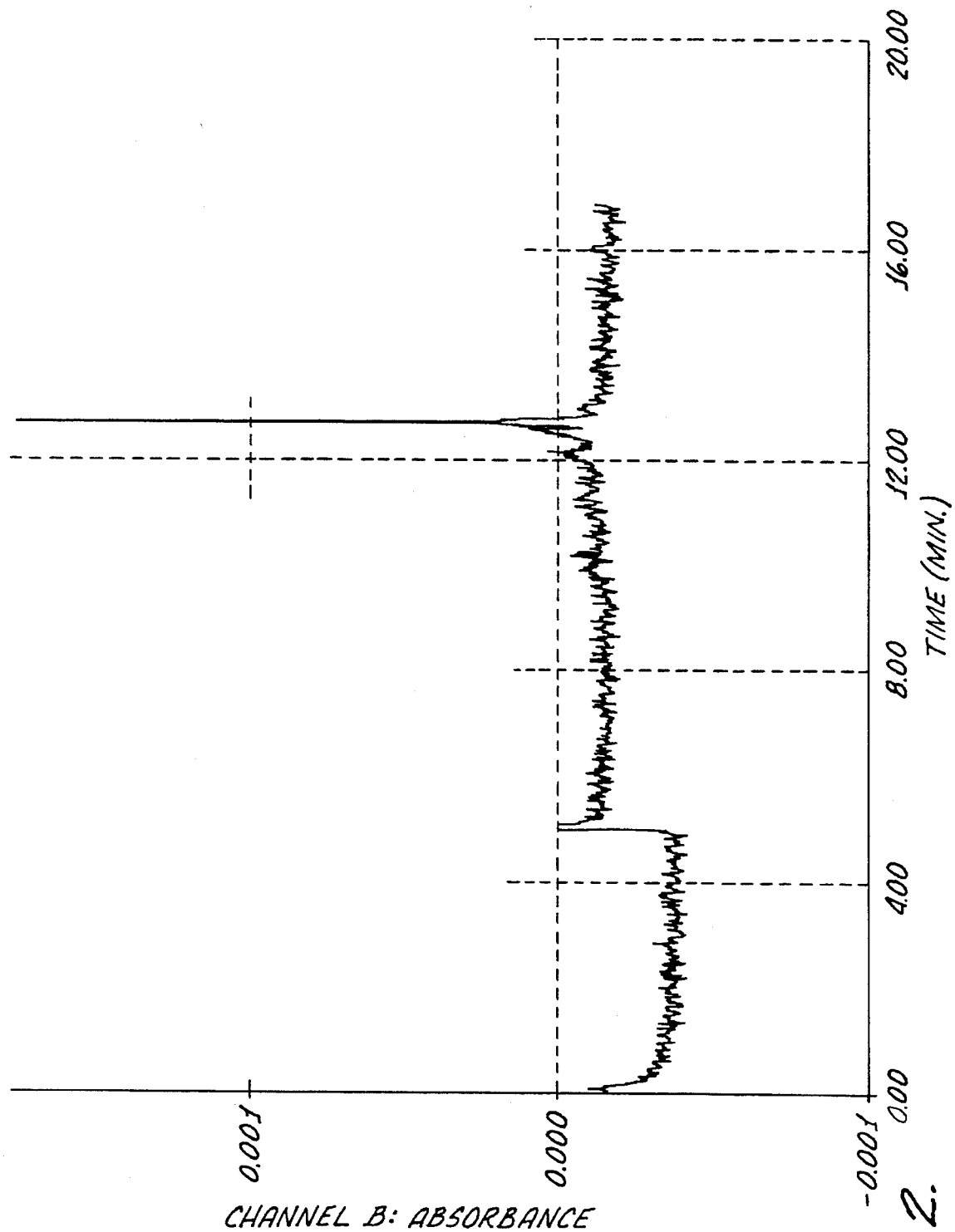
FIG. 2 is the result of Capillary Gel Electrophoresis analysis of the 17-mer oligonucleotide of FIG. 1, with the DMT group having been removed prior to analysis.

As is evident from FIGS. 1 and 2, a single, well defined peak is set forth, indicating, inter alia, that synthesis efficiency on the aminated polypropylene was optimal (the small peak in FIG. 1 is attributed to benzamide formed by the removal of benzoyl protecting groups on the synthetic DNA strand).

EXAMPLE III

Dehybridization Chracteristics of Complements and Mutations

In order to determine the hybridization characteristics of polynucleotides to target sequences synthesized onto aminated polypropylene, a series of experiments were performed using oligonucleotides which had sequences which were perfect complements (i.e. analogous to "wild-type") and sequences which were not perfect complements (i.e. analogous to "mutations"). As noted, in genetic analysis, it is critical to differentiate between wild-type and mutation sequence; this goal is exacerbated given the ability of deleterious mutations to be considered by a single base deletion/substitution and the preonderance of such a mutated sequence to hybridize to a wild-type complement probe. Because of these factors, dehybridization from the target was analyzed over time using the D-HAS™ System.

Previously referenced Target A was directly synthesized onto aminated polypropylene membranes using the aforementioned DNA synthesizer. Thereafter, P23 (perfect compliment to Target A); P24 (single base mismatch); and P37 (two-base deletion) were separately introduced to Target A as follows: aminated polypropylene having Target A covalently bound thereto was equilibrated in Hybridization Buffer; thereafter, each of the three probes (0.5 pmoles/50 μl Hybridization Buffer) were added to these membranes followed by 1 hour incubation at 25° C. Hybridization Buffer was then removed, and membranes rinsed once with 200 μl Hybridization Buffer; thereafter, membranes were added to the D-HAS™ System as disclosed. Analysis of decreasing presence of labelled probes was conducted, with results being collectively presented in FIG. 3.

Figure 3:
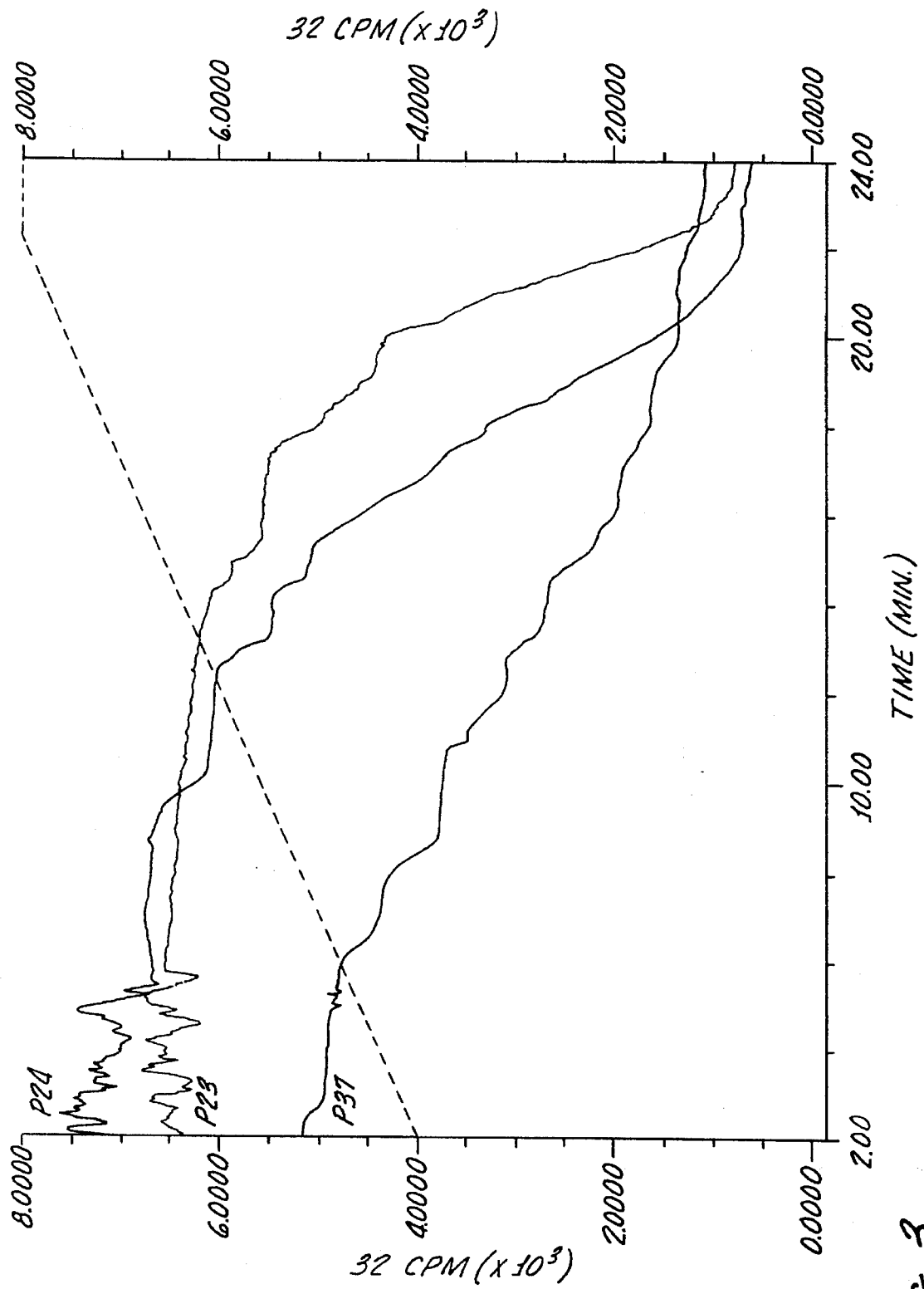
FIG. 3 is the compilation of dehybridization analyses of three oligonucleotide probes from a defined Target Oligonucleotide, the Target Oligonucleotide having been synthesized directly onto aminated polypropylene, each of the probes having various sequences which are complementary or non-complementary to the Target.

It would be expected that between a "perfect" complement to Target A and a "non-perfect" complement, the perfect complement should remain hybridized to Target A longer than the non-perfect complement under identical conditions. FIG. 3 evidences the validity of this expectation. It is noted that the difference in dehybridization patterns between P23 (the complement) and P24 (single base mismatch) is quite evident; the difference in dehybridization patterns between P23 and P37 (two-base deletion) is even more striking.

These results indicate, inter alia, that wild-type target and mutation target(s) can be synthesized directly to aminated polypropylene and these can be used for genetic screening—the ability to differentiate between the presence of wild-type complement and mutation (or vice-versa) is evident.

EXAMPLE IV

Analysis of Cystic Fibrosis ΔF508 Exon 10

Amplicons derived from CRTR Exon 10, ΔF508 patient sample (SEQ ID NO. 8) and CFTR Exon 10, normal patient sample (SEQ ID NO. 7) were provided by Professor C. Thomas Caskey (Baylor Medical College, Houston, Tex.). These were amplified using the sense and antisense primers described; following amplification, biotinylated amplicons were removed (using avidin coated beads) such that substantially only labelled amplicons were utilized for analysis.

Focusing on CFTR Exon 10, the underlined portion of that Sequence (SEQ ID NO. 7) is referred to herein as the "regional mutation," i.e. in ΔF508, the bases CTT are deleted such that ATC TTT is presented as ATT. We have determined that in constructing a target for the regional mutation to be synthesized onto the surface activated organic polymer, it is preferred that the complement to the regional mutation along the target should be located so as to maximize the number of possible mis-matches when the mutation is present. For example, if the regional mutation is located along the target distal to the aminated polypropylene, then the corresponding hybridizations of, in this example, Exon 10,ΔF508 and Exon 10,Normal, are as follows: (the underlined portion is the complement to the regional mutation):

```
3' TTC T TTT ATA GTA GAA   5'    Target A70
5' AAG A AAA TAT CAT CTT   3'    Exon 10, Normal
5' AAG A AAA TAT CAT [TGG] 3'    Exon 10, ΔF508
```

Thus, focusing on Exon 10,ΔF508, along the 16-mer Target A70, when Exon 10,ΔF508 hybridizes thereto, there will be 13 complementary bases, and 3 mis-matches (indicated in brackets). By shifting the complement to the regional mutation toward the polymer, the number of mis-matches increases:

```
3' TTTATAGTAGAAACCA - 5'    Target A61
5' AAATAACATCTTTGGT - 3'    Exon 10, Normal
5' AAATAACAT[TGGTGT]T - 3'  Exon 10, ΔF508
```

This shift decreases the number of complementary bases on a Target A61-Exon 10,ΔF508 hybridization to 10, and increases the number of mis-matches to 6, i.e. a 100% increase in mis-matches.

The intent is that the number of mis-matches should be maximized. This will, of course, depend upon the length of the regional mutation. However, a preferred percentage of mis-matches between a wild-type complement target and a sample mutation is at least about 20%, more preferably about 40%, and most preferably less than about 50% (if the number of mis-matches bases exceeds about 50%, stringency conditions may not allow for sufficient hybridization of a mutation to the target). However, these percentages are relative to the position of the mismatch on the target and the type of mismatch. For example, distal mismatches are less preferred than internal mismatches, and the G-C content involved in the complementary hybridization are typically "stronger" than A-T content.

For the analysis of the Exon 10,ΔF508 and Exon 10,Normal amplicons, Target A61 was utilized; Target A61 was synthesized directly onto aminated polypropylene as described above. Hybridization and dehybridization conditions were as set forth in Example III. Results are presented in FIG. 4.

Figure 4:
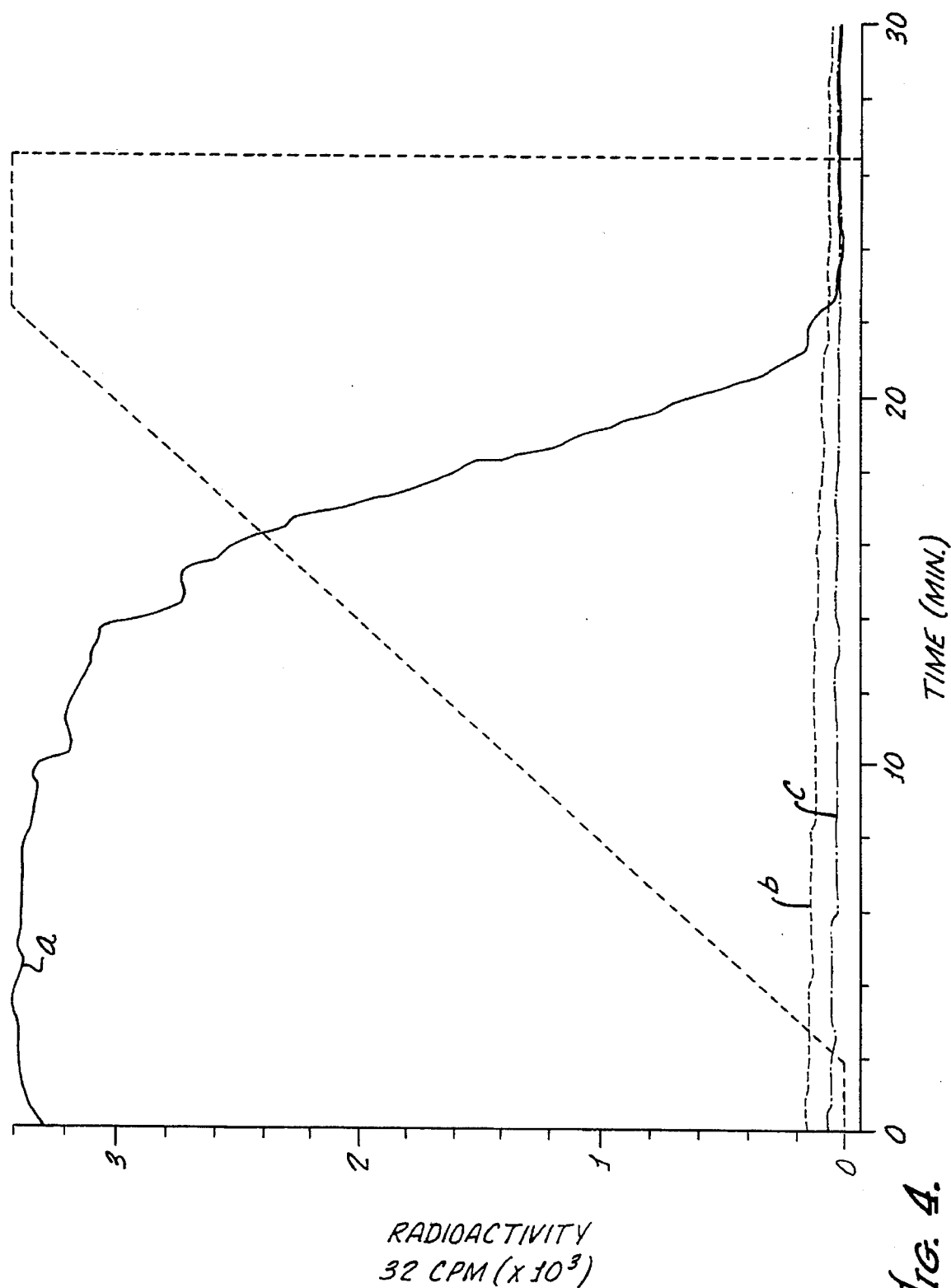
FIG. 4 is the compilation of dehybridization analyses of amplicons from CTFR Exon 10, Normal and CTFR Exon 10, ΔF508, against Target Oligonucleotide complementary to CTFR Exon 10, Normal, the Target Oligonucleotide having been synthesized directly onto aminated polypropylene.

As the results of FIG. 4 indicate, the difference in dehybridization between the CFTR Exon 10, Normal and CFTR Exon 10,ΔF508 from the wild-type complement Target A61 is striking—the pattern for the dehybridization of Exon 10, ΔF508 is nearly identical to that for background noise. Thus, analysis of samples for the presence of genetic mutations can be readily accomplished.

EXAMPLE V

Analysis of Hen-Egg Lysozyme ("HEL") Peptides

The following peptides were synthesized directly onto separate aminated polypropylene membranes. These hen-egg lysozyme peptides had the following sequences:

HEL 11-25 (SEQ. ID. NO. 12):

Ala—Met—Lys—His—Gly—Leu—Asp—
Asn—Tyr—Arg—Gly—Tyr—Ser—Leu

HEL 106-116 (SEQ. ID. NO. 13):

Asn—Ala—Trp—Val—Ala—
Trp—Arg—Asn—Arg—Cys—
Lys

The carboxyl-group of Leu (HEL 11-25) and Lys (HEL 106-116) were coupled directly to the aminated polypropylene (i.e. Leu and Lys, respectively, were the initiator biomonomers). The peptide synthesis was conducted in accordance with the general protocol described in D. Hudson; *J. Org. Chem.* 53:617 (1988); *Milligen Technical Note* 4–30, (1987). Fmoc-protected amino acids were obtained from Beckman Instruments, Inc. (Prod. Nos. Fmoc Cys (Trt): 266366; Fmoc Lys (TBoc): 266387; Fmoc Asn: 266351; Fmoc Trp: 266408; Fmoc Ala: 266342; Fmoc Val: 266414; Fmoc Leu: 266384; Fmoc Ser (OTBu): 266402;

Fmoc Tyr (OTBu): 266410; Fmoc Gly: 266375; Fmoc Asp (OTBu): 266354; Fmoc His (Trt): 266377; Fmoc Met: 266390; Fmoc Arg (Mtr) was obtained from Milligen (Prod. No. 911014). Coupling reagent (1,3-di-isopropyl carbodiimide) was obtained from Aldrich (Prod. No. D12, 540-7). Coupling agent (hydroxybenzotriazole) was obtained from Aldrich (Prod. No. 15,726-0). Fmoc-deblocking group (piperidine) was obtained from Aldrich (Prod. No. 10,409-4). Side-chain groups were removed using 19 ml trifluoro acetic acid (95%) (Aldrich, Prod. No. 29,953-7), 0.5 ml anisole (Aldrich, Prod. No. 12,322-6) and 0.5 ml ethyl methyl sulfide (Aldrich, Prod. No. 23,831-7), which were added to the mixture and left at room temperature for six hours, followed by washing with ether.

To validate the presence of these particular peptides, murine anti-HEL-11-25 monoclonal antibody and murine anti HEL-106-116 monoclonal antibody were utilized in an ELISA format. Antibodies were graciously provided by Dr. Clifford Olson, Beckman Instruments, Inc. These antibodies do not cross-react with these peptides. Three conditions were analyzed: A - aminated polypropylene membrane comprising the HEL-11-25 peptide directly synthesized thereon; B - aminated polypropylene membrane comprising the HEL-106-116 peptide directly synthesized thereon; C - control (aminated polypropylene membrane). ELISA conditions were as follows: the membranes were placed into six individual wells of a 96-well titer plate; two wells comprised membrane/HEL-11-25; two wells comprised membrane/HEL-106-116; and two wells comprised membrane. The following conditions were utilized for each well. A solution of 1% BSA was added to each well, followed by room temperature incubation for 1 hr. This was followed by 3×250 µl washings with phosphate-buffered saline ("PBS"). The anti-HEL-11-16 was added to one well from each set and the anti-HEL-106-116 was added to one well from the remaining set. Thereafter, 100 µl of goat-anti-mouse antibody conjugated with alkaline phosphatase (1:5000 dilution) (High Clone, Utah, Part #EA 1055-X) was added to each well. This was followed by room temperature incubation for 30 min; thereafter, 3×250 µl PBS washings were conducted. Afterwards, 100 µl of NBT-BCIP (nitro blue tetrazolium -Sigma N6876; 5-bromo-4-chloro-3-indolyl-phosphate-Sigma, B6149 prepared as follows: 66 µl of NBT stock (0.5 g of NBT in 10 ml of dimethylformamide) and 33 µl of BCIP stock (0.5 g of BCIP in 10 ml of 70% dimethylformamide) added to 10 ml of alkaline phosphatase buffer (100 mm NaCl; 5 mm $MgCl_2$; 100 mm tris-hydroxymethyl aminomethane, pH 9.5)) solution was added to each well. A 10 min period for color (blue) development was allotted. Thereafter, the wells were washed with deionized water. The presence of blue color following the washing indicated the presence of goat-anti mouse bound to the monoclonal antibodies (results not presented).

The respective antibodies bound specifically to their respective peptides. E.g., no blue color was observed in the wells comprising membrane/HEL-11-16 and aminated polypropylene to which was added anti-HEL-106-116. No color in the aminated polypropylene indicates that non-specific binding of either antibody did not occur. The specific binding of the antibodies to specific peptides indicates, inter alia, that the HEL-11-25 and HEL-106-116 peptides were indeed correctly synthesized onto the aminated polypropylene.

EXAMPLE VI

Dipstick Hybridization

Aminated 1.2 mil biaxially oriented polypropylene film having SAM 125 covalently attached thereto was soaked for 10 min in Hybridization Buffer. Thereafter, 3 µl 615 Fluorescent Probe in 97 µl Hybridization Buffer (100 pmol/100 µl) was added thereto, followed by incubation for 90 min. This was followed by 4×200 µl washings with Hybridization Buffer. The film was then removed and placed onto a glass slide, followed by analysis using the CCD camera; a laser-printer reproduction of the results are presented in FIG. 5.

Figure 5:
FIG. 5 is a laser-printer reproduction of a hybridization between a fluorescent-labelled probe and a target synthesized directly onto aminated polypropylene, with detection of the label via a CCD camera.

The results of FIG. 5 indicate that strong hybridization occured between SAM 125 and 615 Flourescent Probe. The length of the probe vis-a-vis the target did not interfere with hybridization. This dip-stick format allows for rapid analysis for the presence or absence of a genetic mutation of interest; the use of non-radiactive labels avoids certain concerns raised by the use of radioactive labels.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims.

What is claimed is:

1. In a method for synthesizing biopolymer attached to a solid support material, said method comprising sequentially coupling biomonomers to form said biopolymer, wherein the improvement comprises sequentially coupling biomonomers to a solid support material formed of biaxially oriented polypropylene having nucleophiles linked to its surface.

2. The method of claim 1 wherein the nucleophiles are selected from the group consisting of amine, hydroxyl, thiol, and carboxylate.

3. The method of claim 1 wherein the biopolymer is selected from the group consisting of oligonucleotides, proteins, peptides, oligosaccharides, lipids, phospholipids, avidin, analogues of the foregoing, and combinations of at least two of the foregoing.

4. The method of claim 1 wherein the surface of the biaxially oriented polypropylene comprises an amine.

5. The method of claim 1 wherein the surface of the biaxially oriented polypropylene comprise an hydroxyl.

6. The method of claim 1 wherein the surface of the biaxially oriented polypropylene comprise a thiol.

7. The method of claim 1 wherein the biopolymer is selected from the group consisting of oligonucleotides, peptides and oligosaccharides.

8. In a method for synthesizing biopolymer attached to a solid support material, said method comprising sequentially coupling biomonomer to form said biopolymer, wherein the improvement comprises sequentially coupling biomonomers to a solid support formed of material selected from the group consisting of hydroxylated biaxially oriented polypropylene, aminated biaxially oriented polypropylene, and thiolated biaxially oriented polypropylene.

9. The method of claim 8 wherein the biopolymer is selected from the group consisting of oligonucleotides, peptides and oligosaccharides.

10. In a method for the sequential analysis of a protein or a peptide, the method comprising attaching the protein or peptide to a solid support and sequentially cleaving amino acids from an N-terminus of the peptide, wherein the improvement comprises attaching the protein or peptide to a nucleophile to the surface of an organic polymer, wherein the polymer is biaxially oriented polypropylene.

11. The method of claim 10 wherein the nucleophile is selected from the group consisting of amine, hydroxyl, thiol, and carboxylate.

12. A method of analyzing an oligonucleotide of interest comprising the steps of:

(a) providing an organic polymer device comprising nucleophiles adsorbed onto the surface thereof wherein at least one attached oligonucleotide having a defined sequence is covalently attached to the polymer device via the nucleophiles and the polymer is biaxially oriented polypropylene;

(b) applying the oligonucleotide of interest to the organic polymer device under conditions suitable for the oligonucleotide of interest to hybridize to the at least one attached oligonucleotide, said oligonucleotide of interest having a fluorescent label; and (c) determining if said oligonucleotide of interest has hybridized in a complementary manner to the attached oligonucleotide said determining accomplished by detecting said fluorescent label.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
CAACATTTCG GTTGTG                                                      16
```

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
GGTGTAAAGC CAACAC                                                      16
```

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
GGTGTAAGGC CAACAC                                                      16
```

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
GGTGTAAACA ACAC                                                        14
```

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
TTTATAGTAG AAACCA                                                      16
```

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

TTCTTTTATA GTAGAA      16

( 2 ) INFORMATION FOR SEQ ID NO:7:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GTTTTCCTGG ATTATGCCTG GCACCATTAA AGAAAATATC ATCTTGGTG TTTCCTATGA    60

TGAATATAGA TACAGAAGCG TCATCAAAGC ATGCCAA    97

( 2 ) INFORMATION FOR SEQ ID NO:8:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GTTTTCCTGG ATTATGCCTG GCACCATTAA AGAAAATATC ATTGGTGTTT CCTATGATGA    60

ATATAGATAC AGAAGCGTCA TCAAAGCATG CCAAC    95

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GTTTTCCTGG ATTATGCCTG GCAC    24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:10:

GTTGGCATGC TTTGATGACG CTTC        24

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TCAGCTACCG TAAATGT        17

( 2 ) INFORMATION FOR SEQ ID NO:12:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:12:

Ala Met Lys Arg His Gly Leu Asp Asn Tyr Arg Gly Tyr Ser Leu
    1                5                      10                    15

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

Asn Ala Trp Val Ala Trp Arg Asn Arg Cys Lys
    1                5                      10

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear

```
        ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

AAGGACCTAA   TACGG                                                        15

( 2 ) INFORMATION FOR SEQ ID NO:15:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

GTTTCCTGG   ATTATGCCTG   GCAC                                             24
```